(12) United States Patent (10) Patent No.: US 8,150,713 B2
Clements et al. (45) Date of Patent: *Apr. 3, 2012

(54) PHARMACEUTICAL TREATMENT EFFECTIVENESS ANALYSIS COMPUTER SYSTEM AND METHODS

(75) Inventors: Leon Clements, League City, TX (US); Glenn G. Hammack, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/838,315

(22) Filed: Jul. 16, 2010

(65) Prior Publication Data

US 2010/0280846 A1 Nov. 4, 2010

Related U.S. Application Data

(63) Continuation of application No. 10/959,627, filed on Oct. 6, 2004, now Pat. No. 7,761,311, which is a continuation-in-part of application No. 10/806,878, filed on Mar. 23, 2004, now Pat. No. 7,813,939.

(51) Int. Cl.
*G06F 19/00* (2011.01)
(52) U.S. Cl. .............................................. 705/3; 705/2
(58) Field of Classification Search ................... 705/2–3
See application file for complete search history.

(56) References Cited

U.S. PATENT DOCUMENTS

| | | | |
|---|---|---|---|
| 4,036,462 A | 7/1977 | Sheftel | |
| 4,193,114 A | 3/1980 | Benini | |
| 4,525,775 A | 6/1985 | Eydelman | |
| 4,857,713 A | 8/1989 | Brown | |
| 5,291,399 A | 3/1994 | Chaco | |
| 5,377,258 A | 12/1994 | Bro | |
| 5,619,991 A | 4/1997 | Sloane | |
| 5,758,095 A | 5/1998 | Albaum | |
| 5,911,132 A | 6/1999 | Sloane | |
| 5,933,136 A * | 8/1999 | Brown | 715/741 |

(Continued)

FOREIGN PATENT DOCUMENTS

EP 0 510 615 A1 4/1992

(Continued)

OTHER PUBLICATIONS

Rainer, Ben G. MD and Stobo, John D., MD; Health Care Delivery in the Texas Prison System, The Role of Academic Medicine, JAMA—The Journal of the American Medical Association; Jul. 28, 2004; pp. 485-489, vol. 292, No. 4 U.S. Clements, et al.; Presentation titled "CyberCare A. Medical Delivery for the Future"; presented at The National Healthcare Congress in Miami, FL., Nov. 6, 1999.

(Continued)

*Primary Examiner* — Gerald J. O'Connor
*Assistant Examiner* — Hiep V Nguyen
(74) *Attorney, Agent, or Firm* — Wong Cabello Lutsch, Rutherford & Brucculeri, LLP

(57) ABSTRACT

Computer-implemented systems, program code, and related methods are provided. The systems, program code, and methods can be employed to analyze the effectiveness of pharmaceutical treatments for medical conditions utilizing real time prescription compliance records. Information related to medical history of a patient can be reviewed while simultaneously reviewing prescription compliance records for the same patient. Trends in target and non-target medical parameters can be identified and correlated with the prescription compliance records to determine the effectiveness of a pharmaceutical treatment on target and non-target medical parameters that various compliance and prescription levels.

20 Claims, 12 Drawing Sheets

U.S. PATENT DOCUMENTS

| | | | |
|---|---|---|---|
| 6,152,364 A | 11/2000 | Schoonen | |
| 6,369,847 B1 | 4/2002 | James | |
| 6,587,829 B1* | 7/2003 | Camarda et al. | 705/3 |
| 6,666,820 B1 | 12/2003 | Poole | |
| 7,129,970 B2 | 10/2006 | James | |
| 7,278,028 B1 | 10/2007 | Hingoranee | |
| 2002/0120471 A1 | 8/2002 | Drazen | |
| 2003/0036683 A1 | 2/2003 | Kehr | |
| 2003/0036923 A1* | 2/2003 | Waldon et al. | 705/2 |
| 2003/0050799 A1 | 3/2003 | Jay | |
| 2003/0050802 A1 | 3/2003 | Jay | |
| 2004/0088187 A1 | 5/2004 | Chudy | |
| 2004/0138921 A1 | 7/2004 | Broussard | |
| 2004/0193019 A1 | 9/2004 | Wei | |

FOREIGN PATENT DOCUMENTS

| | | |
|---|---|---|
| EP | 1 237 113 A2 | 4/2002 |
| WO | 9941014 | 8/1999 |
| WO | 2004015602 A2 | 2/2004 |

OTHER PUBLICATIONS

Article titled Innovative Programs in Telemedicine, University of Texas Medical Branch at Galveston Electronic Network, Telemedicine and e-Health, vol. 11, No. 2, 2005.

Bouabene, A.; Article titled "Providing Emergency Medical Care to Offshore Oil and Gas Platforms in the Gulf of Mexico using Telemedicine," Applications of Broadband Optical and Wireless Networks, Proceedings of SPIE, vol. 4912 (2002) XP-0002396166.

UTMB Correctional Managed Care uses Cyb-R Care to provide remote physician services across the State of Texas, Booth Presentation, May 10, 2001.

Towards the Electronic Patient Record (TEPR), Using the Electronic Medical Record to Support Telemedicine, May 11, 2001.

Telemedicine, An Introduction, Review, and Considerations, HI 2001, May 16, 2001.

American Telemedicine Association (ATA), PowerPoint Presentation, for Lauderdale, Florida, Jun. 5, 2001.

Business Computer Applications and the University of Texas Medical Branch Correctional Managed Care welcomes Representatives of the U.S. Federal Bureau of Prisons Washington, D.C., Aug. 14, 2001.

Digital Medical Services Telemedicine/EMR update, VA-HHS, Aug. 15, 2001.

Digital Medical Services Telemedicine/EMR Update, ACA Philly, Aug. 23, 2001.

Digital Medical Technology Overview, Enron, Sep. 6, 2001.

Allen, John; UTMB Correctional Managed Care Private Prison Presentation, www.digitalmedicalservices.com; Private Prisons, Dec. 12, 2001.

Using the Emerald Reports Screens, Dec. 19, 2001.

UTMB Electronic Medical Records and Telemedicine in the Correctional Environment, www.digitalmedicalservicescom; American Correctional Association, Workshop A-2, San Antonio, Jan. 12, 2002.

UTMB Electronic Medical Records and Telemedicine in the Correctional Environment; Pfizer 2002, Jan. 13, 2002; www. digitalmedicalservices.com; American Correctional Association, Workshop A-2, San Antonio.

UTMB State of the Art Telemedicine and Electronic Medical Records in the Corrections, www.digitalmedicalservices.com; America Correctional Health Services Association (ACHSA); Portland; Mar. 16, 2002.

UTMB Digital Medical Services, Overview, Federal Bureau of Prisons Visitors, www.digitalmedicalservices.com; Mar. 27, 2002.

UTMB Digital Medical provides remote physician services across the State of Texas, Digital Medical Services (DMS) Booth 2, May 14, 2002.

Towards the Electronic Patient Record (TEPR), UTMB Correctional Managed Care Information Services, Design and Performance of the UTMB CMC Statewide EMR System, May 14, 2002.

UTMB Correctional Managed Care Uses +DMS to provide remote physician service across the State of Texas; Jun. 3, 2002.

UTMB Correctional Managed Care Information Services, Future Management of EMR Implementation and Development, A Proposal to CMC Administration, Summer Quarterly Management Meeting, Open Gates, Galveston, Texas; Jul. 10, 2002.

UTMB Correctional Managed Care Information Services. The Primary Care Studio in Galveston, Texas; Administration Systems, Aug. 14, 2002.

UTMB Correctional Managed Care Information Services, Optometric Education of the Future TELEMEDICINE, American Society of Clinical Oncology (ASCO) Telemed; Oct. 4, 2002.

UTMB Correctional Managed Care Information Services, A Common Electronic Medical Record for TDCJ Unit Clinics, Tech Lubbock, Oct. 18, 2002.

UTMB Correctional Managed Care Uses +DMS to provide remote physician service across the State of Texas: +DMS Booth Presentation LMC; Oct. 27, 2002.

UTMB Correctional Managed Care Uses +DMS to provide remote physician services across the State of Texas; www. digitalmedicalservices.com; +DMS Booth, Jan. 29, 2003.

UTMB Correctional Managed Care (CMC) Electronic Medical Record (EMR) and Digital Medical Services (DMS); Dallas County Commissioners; Mar. 26, 2003.

UTMB Correctional Managed Care Uses +DMS to provide remote physician service across the state of Texas; www. digitalmedicalservices.com; +DMS Booth; Aug. 12, 2003.

UTMB Correctional Managed Care (CMC) Information Systems, Electronic Medical Record (EMR) and Digital Medical Services (DMS); www.digitalmedicalservices.com; Centers for Disease Control (CDC), Business Computer Applications (BCA); Sep. 9, 2003.

UTMB Correctional Managed Care (CMC) Information Systems, Real IP Telemedicine: A Sustained Model, www. digitalmedicalservices.com; Polycom TM; Oct. 7, 2003.

UTMB Correctional Managed Care (CMC) Information Systems; The Role of the Community Physician in the Evolving Landscape of e-Health or How We Fit Primary Care Services into and Active, Sustained Telemedicine Practice; www.digitalmedicalservices.com; Nov. 10, 2003.

UTMB Telemedicine in Managed Care; www. digitalmedicalservices.com; Nov. 11, 2003.

Electronic Medical Records (EMR) Leadership Retreat; Texas Tech Kickoff Leadership; Huntsville, Texas; Dec. 16, 2003.

Studio Spinners, Apr. 10, 2004.

UTMB Correctional Managed Care (CMC) Information Systems; Digital Medical Systems (DMS) Cardiology, American Telemedicine Association (ATA) Cardio; Apr. 16, 2004.

UTMB Correctional Managed Care (CMC) Information Systems, Telemedicine (TM) Nuts and Bolts; Correctional Health Long Course; American Telemedicine Association (ATA); May 2, 2004.

*The University of Texas Medical Branch* vs. *Emtel, Inc.*; Civil Action H-03-0889; Complaint for Declaratory Judgment, filed Mar. 11, 2003; United States District Court, Southern District of Texas; Houston Division.

UTMB, The University of Texas Medical Branch, Telemedicine Digital Medical Services, and the UTMB Electronic Health Network, presentation, Mar. 2005.

UTMB, Electronic Health Network, Remote Physician Services Telemedicine Proposal, Jul. 14, 2005.

Letter dated Sep. 13, 2002, from Emtel, Inc. to UTMB and P&O Cruises, regarding U.S. Patent 6,369,847.

Carmenates, Janet and Keith, Matthew R.; Article entitled "Impact of Automation on Pharmacist Interventions"; pp. 1-4; Am. J. Health-Syst Pharm 58(9):779-783 2001; www.medscape.com/viewarticle/406963.

Bonnabry, Dr. Pascal; A report by Pascal Bonnabry, Chief Pharmacist, University Hospitals of Geneva and Head, Information Systems, Swiss Society of Public Health Administration and Hospital Pharmacists (GSASA); pp. 1-5; Business Briefing: European Pharmacotherapy 2003.

International Search Report dated Jan. 23, 2006.

Related U.S. Appl. No. 10/806,878.

Related U.S. Appl. No. 10/959,627.

\* cited by examiner

FIG. 6.

PHARMACEUTICAL TREATMENT EFFECTIVENESS ANALYSIS COMPUTER SYSTEM AND METHODS

RELATED APPLICATIONS

This application is a continuation application of and claims priority to and the benefit of U.S. patent application Ser. No. 10/959,627 filed Oct. 6, 2004, titled "Pharmaceutical Treatment Effectiveness Analysis Computer System and Methods," which is a continuation-in-part of and claims priority to and the benefit of U.S. patent application Ser. No. 10/806,878, filed on Mar. 23, 2004, titled "Pharmaceutical Inventory and Dispensation Computer System and Methods."

BACKGROUND OF THE INVENTION

1. Field of the Invention

The present invention relates to computer-implemented methods, program code, program devices, and systems for analyzing the effectiveness of pharmaceutical treatments and, more specifically, for determining the effectiveness of pharmaceutical treatments utilizing real time prescription compliance records.

2. Description of the Related Art

Clinical studies have been used for many years to help the medical industry determine or verify the effects of pharmaceutical treatments on human subjects having various ailments or medical conditions. Clinical studies are typically conducted by universities or hospitals that are either trying to determine how a certain drug or pharmaceutical treatment affects a patient with a particular medical condition or how a certain medical condition can be affected by various pharmaceutical medication and treatments. Other purposes of clinical studies can also include determining side effects of treatment, determining if the benefits outweigh the side effects of the treatment, and determining which patients the treatment is most likely to help.

Before a medication can be sold to consumers, either over-the-counter or through a prescription, the medication must be rigorously tested on human subjects. To be eligible for approval by the Food and Drug Administration (FDA), a medication must be studied, typically in three clinical trial phases. The purpose of the first phase, or Phase I, clinical study is to determine the safety of the medication. In Phase I clinical studies, a goal is to find the best way to give a new treatment and how much of it can be given safely. Study administrators, who are often physicians, typically monitor patients very carefully, often in a hospital setting, for any harmful side effects. At this point, the pharmaceutical treatment has been well tested in laboratory and animal studies, but the side effects in humans are not completely known. Study administrators usually start by giving very low doses of the pharmaceutical treatment to the first patients and increasing the dose for later groups of patients until side effects appear. Although study administrators are hoping to help patients, the main purpose of such a Phase I study is to test the safety of the pharmaceutical treatment. Some Phase I clinical trials are designed to fine-tune a regimen such as combining two well known drugs before going into Phase II studies, and although the safety is being established, such studies usually give drug doses that have already been shown to be at least partially effective.

Once a medication has been determined to be safe in human subjects, such as by Phase I testing, the pharmaceutical treatment must then be tested in the patients that have the target disease or medical condition that the pharmaceutical treatment is expected to help or cure. This phase, Phase II, of the clinical studies typically includes ensuring the safety and effectiveness of the pharmaceutical treatment in the patient population of interest. Generally, patients are given the highest dose that does not cause severe side effects, which is based on the results of the Phase I study, and closely observed for an effect on the target disease or medical condition at issue. Study administrators will also look for additional side effects that may be present in this group of patients having the disease or condition at interest.

In Phase III clinical studies, the pharmaceutical treatment is given to a much larger patient population of interest. Some clinical studies can enroll thousands of patients. The large-scale testing enables doctors to understand the effectiveness of the pharmaceutical treatment, the benefits and risks of the pharmaceutical treatment, and the range or severity of possible adverse side effects.

Several problems exist with current clinical studies. One problem is that the subjects of the study are typically not monitored on a continuous basis. The subjects periodically check in and have various tests performed to determine if the pharmaceutical treatment has had any affect on their medical condition. The subject is typically asked if they have been taking their pharmaceutical treatment, as prescribed. If subjects have not been taking the pharmaceutical treatment as prescribed and yet indicate that they have been taking the treatment as prescribed, then the results of the clinical study are not accurate. To compound the problem, many subjects are paid for their participation in the study, which provides an incentive for the subject to tell the study administrator that they have been taking the treatment as prescribed, when in fact they have not.

With some treatments, if the subject does not take the pharmaceutical treatment as prescribed at least a preselected portion of the time, i.e., 15% of the time, the pharmaceutical may actually have adverse effects on the subject. Without actual data regarding how often the subject took the pharmaceutical treatment, it is difficult to determine with certainty the effectiveness of the pharmaceutical treatment.

Another drawback of conventional clinical studies is that typically only the targeted parameter is monitored, as opposed to the overall health of each clinical study. For example, if a hospital is trying to determine the effectiveness of a new cholesterol reducing medication, typically only the cholesterol will be monitored on the subject. If the treatment made the subject's resting heart rate lower, this may not be recognized or noticed by the clinical administrator. Various treatments may affect more than the targeted parameter. Without continuous overall health monitoring, the side effects other than with regard to the targeted parameter may not be noticed by the clinical administrator.

Correctional facilities have a large population of inmates that have various medical conditions that require constant medical monitoring and administration of pharmaceutical treatments. Correctional facilities closely monitor and track medical conditions through the use of such systems as electronic medical records, as described in co-pending U.S. patent application Ser. No. 10/806,878, of which the present application is a continuation-in-part. The electronic medical records have been used to record such events as provider visit results, prescription histories, lab work results, and the like. The electronic medical records typically have been developed and maintained either by the correctional facilities or by a third party that has been providing healthcare services for the correctional facility system.

Medicinal administrators within correctional facilities are also required to maintain records associated with the physical administration and dispensation of prescribed pharmaceutical treatment to inmates. Inmates by law must have proper medical care while in the custody of the correctional facilities. To provide sufficient evidence that the correctional facilities have exerted their best efforts to provide proper medical care, the correctional facilities have maintained records indicating the time, type, and dosage of each pharmaceutical treatment that was administered to an inmate. A guard has been present during pharmaceutical treatment administration to ensure that the inmates actually consumed their prescribed pharmaceutical treatments, unless, as in rare circumstances, the inmates were allowed to keep the medication on their person, referred to as "keep-on-person" medication. The correctional facility has kept records indicating whether or not the inmate has actually took the pharmaceutical treatment. Many times the records are either paper based or kept on a standalone computer system. Since the implementation of such methods and systems the number of grievances filed by inmates has drastically reduced.

Clinical studies have been performed on inmates who volunteered to be test subjects in the studies. Problems existed in the past because there was no guarantee that the inmate took the pharmaceutical treatment as prescribed.

SUMMARY OF THE INVENTION

In view of the foregoing, various embodiments of the present invention advantageously feature computer implemented systems, program devices, program code, and computer implemented methods which analyze the effectiveness of pharmaceutical treatments for medical conditions which utilizes trend data for target and non-target medical parameters (physiological conditions) correlated with real-time prescription compliance data, for example, reflecting actual observed consumption (or non-consumption) by a patient of a pharmaceutical substantially as prescribed—i.e., the prescribed pharmaceutical at the prescribed time or interval and in the prescribed quantity. Various embodiments of the present invention also advantageously provide computer implemented systems, program code, program devices, and methods which provide computerized monitoring of effectiveness of pharmaceutical treatments in patients in conjunction with computerized electronic medical records stored in a computer memory. The electronic medical records preferably contain information about the patient to receive the pharmaceutical treatment under evaluation, information about the patient's medical history, and a prescription compliance record. The prescription compliance record preferably contains information about a frequency in which the patient complied with prescription instructions for the pharmaceutical treatment. The pharmaceutical treatment can be an experimental medication, an existing medication, prescription medication, over-the-counter medication, non-medicinal treatments, or combinations thereof.

More specifically, an embodiment of the present invention, includes a method for computerized monitoring of effectiveness of pharmaceutical treatments under evaluation in patients. The method can include the steps of receiving, for each of a plurality of patients, data indicating whether the respective patient self-administered a pharmaceutical treatment under evaluation, as prescribed, storing the received data, and determining a potential effectiveness of the pharmaceutical treatment under evaluation on a target medical parameter.

The step of receiving can be performed, for example, by a computer having access to electronic medical records to thereby document patient compliance with prescription instructions for the pharmaceutical treatment under evaluation. The step of storing the received data can include storing a data entry for each respective patient in a prescription compliance record indicating whether the patient took the pharmaceutical treatment under evaluation, as prescribed, to form the prescription compliance record or medication administration record. The prescription compliance record, which is preferably a database, can provide real-time data about the frequency in which the patient took the pharmaceutical treatment as prescribed. The prescription compliance record allows providers to access real-time data related to the patient's medical dosing status.

The step of determining a potential effectiveness of the pharmaceutical treatment under evaluation can include the steps of analyzing a trend related to the target medical parameter indicating effects of consumption of the pharmaceutical treatment under evaluation by the plurality of patients at a plurality of different pharmaceutical treatment compliance levels at each of one or more constant prescription levels. This can allow a provider to determine a correlation, when existing, between the trend related to the target medical parameter and compliance level associated with the respective one or more constant prescription levels for the pharmaceutical treatment under evaluation, which facilitates determining an effect of compliance level on effectiveness of the pharmaceutical treatment under evaluation at each of the one or more constant prescription levels. For example, according to an exemplary embodiment of the method, once the prescription compliance record is formed, the electronic medical record of the patient can be presented so that a provider can identify trends related to a target medical parameter. Any identified trends in the target medical parameter are presented to the provider for analysis to note correlations in the trends with the prescription compliance record. The noted correlations are then stored in the electronic medical record. The noted correlations are presented to the provider for analysis. Once the doctor or other provider has analyzed the correlations, data entries from the provider's analysis indicating potential effectiveness of the pharmaceutical treatment on the target medical parameter based upon the correlations observed between the target medical parameter and the prescription compliance record are stored in the electronic medical record. The overall health outcome of the patient can also be evaluated, as opposed to only specific medical parameters.

The step of determining a potential effectiveness of the pharmaceutical treatment under evaluation can further include the steps of determining a threshold level of compliance for each of the one or more constant prescription levels below which receiving the pharmaceutical treatment under evaluation at the respective prescription level results in an effect that is less desirable than an effect of not receiving the pharmaceutical treatment under evaluation, and/or determining for each of the one or more constant prescription levels, a minimum level of compliance necessary to have a positive effect on the target medical parameter exceeding that of not receiving the pharmaceutical treatment under evaluation.

According to an embodiment of the present invention, the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter indicating effects of consumption of the pharmaceutical treatment under evaluation by the plurality of patients at each of the plurality of different compliance levels at one or more of the plurality of different prescription levels and/or at each of the plurality of different prescription levels at one or more of the plurality of different compliance levels for each separate one of a plurality of different pharmaceutical treatment dispensation times. Correspondingly, the step of determining a potential effectiveness of the pharmaceutical treatment under evaluation on the target medical parameter can include determining the potential effectiveness of the pharmaceutical treatment under evaluation dispensed at a constant compliance level and/or at a constant prescription level, at each of the plurality of different pharmaceutical treatment dispensation times, to facilitate determining the effects of differing treatment dispensation times across differing levels of compliance and/or prescription amount to identify optimal dispensation times selection at optimal prescription level with respect to anticipated compliance levels.

According to another embodiment of the present invention, the step of analyzing a trend related to the target medical parameter can include analyzing a trend related to the target medical parameter indicating effects of consumption of the pharmaceutical treatment under evaluation by the plurality of patients collectively having a plurality of different demographic factors at each of the plurality of different compliance levels at constant prescription level for each of a plurality of different prescription levels for each separate one of the plurality of demographic factors. Correspondingly, the step of determining a potential effectiveness of the pharmaceutical treatment under evaluation on the target medical parameter can include determining the potential effectiveness of the pharmaceutical treatment under evaluation at each of the plurality of different prescription levels with respect to each separate one of plurality of demographic factors.

As described above, once the prescription compliance record is formed, the electronic medical record of the patient can be presented so that a provider can identify trends related to a target medical parameter. Trends in non-target medical parameters can also be determined if non-target medical parameters are also affected by the pharmaceutical treatment so that trends in an overall health of the patient can also be evaluated. As such, according to another embodiment of the present invention, the method can include the steps of analyzing a trend related to the non-target medical parameter indicating effects of consumption of the pharmaceutical treatment under evaluation by the plurality of patients at the plurality of different pharmaceutical treatment compliance levels at each of the one or more constant prescription levels to thereby determine a correlation, when existing, between the trend related to the non-target medical parameter and compliance level associated with the respective one or more constant prescription levels for the pharmaceutical treatment under evaluation, determining an effect of compliance level on the pharmaceutical treatment under evaluation at each of the one or more constant prescription levels, and determining a potential effectiveness of the pharmaceutical treatment under evaluation on the non-target target medical parameter at each of the one or more constant prescription levels responsive to the determination of an effect of compliance level on the pharmaceutical treatment under evaluation.

Still further, according to another embodiment of the present invention, the method can include the steps of performing an actual physical verification by a human observer that a patient consumed the pharmaceutical treatment under evaluation as prescribed, and storing in memory of the computer, an indication of whether the respective patient self-administered the pharmaceutical treatment under evaluation as prescribed (compliance indication). Note, according to a preferred implementation, the compliance indication includes the indication of the actual physical verification by the human observer that the respective patient consumed the pharmaceutical treatment under evaluation as prescribed. Advantageously, this can help ensure that the compliance indication data is accurate.

Another embodiment of the present invention advantageously includes computer readable code of program instructions stored on a tangible program storage device readable by a computer, that when executed by the computer, cause the computer to perform various operations for computerized monitoring of effectiveness of pharmaceutical treatments under evaluation. The operations can include receiving a data entry for each separate one of a plurality of patients and for each medication administration event and storing the compliance data for each respective patient in a prescription compliance record of the respective patient. Each data entry can include or otherwise provide an indication of whether a patient self-administered the pharmaceutical treatment under evaluation as prescribed to define compliance data to thereby document in a prescription compliance record of each specific patient, information about a frequency in which the patient complied with prescription instructions for the pharmaceutical treatment under evaluation.

The operations can also include processing at least portions of the compliance data, providing data to graphically display to a provider a trend related to a target medical parameter indicating effects of consumption of the pharmaceutical treatment under evaluation by the plurality of patients at a plurality of different pharmaceutical treatment compliance levels at each of one or more constant prescription levels, and storing noted correlations between the trend related to the target medical parameter and compliance level associated with the respective one or more constant prescription levels for the pharmaceutical treatment under evaluation, when existing, responsive to identification of the correlations by the provider.

The operations can also include providing data to graphically display an indication of a presently identified correlation between a trend related to the target medical parameter and compliance frequency for the pharmaceutical treatment under evaluation to thereby aid a provider to determine a threshold level of compliance for each of the one or more constant prescription levels below which receiving the pharmaceutical treatment under evaluation at the respective prescription level results in an effect that is less desirable than an effect of not receiving the pharmaceutical treatment under evaluation, and to thereby aid a provider to determine a minimum level of compliance necessary to have a positive effect on the target medical parameter exceeding that of not receiving the pharmaceutical treatment under evaluation for each of the one or more constant prescription levels responsive to provider analysis of a respective presently identified correlation at each of the of the one or more constant prescription levels.

The operations can further include storing an indication of the threshold level of compliance for each of the one or more constant prescription levels below which receiving the pharmaceutical treatment under evaluation at the respective prescription level results in an effect that is less desirable than an effect of not receiving the pharmaceutical treatment under evaluation, and storing an indication of a minimum level of compliance necessary to have a positive effect on the target medical parameter exceeding that of not receiving the pharmaceutical treatment under evaluation for each of the one or more constant prescription levels responsive to provider analysis of a respective presently identified correlation at each of the of the one or more constant prescription levels.

According to an embodiment of the present invention, the operation of providing data to graphically display to a provider a trend related to a target medical parameter indicating effects of consumption of the pharmaceutical treatment under evaluation by the plurality of patients at a plurality of different pharmaceutical treatment compliance levels at each of one or more constant prescription levels is performed for each separate one of a plurality of different prescription levels. Further, the operation of storing an indication of the threshold level of compliance for each of the one or more constant prescription levels below which receiving the pharmaceutical treatment under evaluation at the respective prescription level results in an effect that is less desirable than an effect of not receiving the pharmaceutical treatment under evaluation includes storing an indication of the threshold level of compliance for each separate one of the plurality of constant prescription levels.

According to an embodiment of the present invention, the operations can also include providing data to graphically display a trend related to a non-target medical parameter indicating effects of consumption of the pharmaceutical treatment under evaluation by the plurality of patients at a plurality of different pharmaceutical treatment compliance levels at each of one or more constant prescription levels to facilitate identifying a correlation, when existing, between the trend related to the non-target medical parameter and compliance level associated with the respective one or more constant prescription levels for the pharmaceutical treatment under evaluation. The operations can further include determining an effect compliance level on the pharmaceutical treatment under evaluation at each of the one or more constant prescription levels, and determining a potential effectiveness of the pharmaceutical treatment under evaluation on the non-target target medical parameter responsive to the determination of the effect compliance level on the pharmaceutical treatment under evaluation at each of the one or more constant prescription levels. Further, the operations can include storing an indication of the potential effectiveness of the pharmaceutical treatment under evaluation on the non-target target medical parameter for each of the one or more constant prescription levels responsive to the determination of an effect of compliance level on the pharmaceutical treatment under evaluation at each of the one or more constant prescription levels.

Another embodiment of the present invention advantageously includes a program storage device readable by a computer, tangibly embodying a computer-readable code of program instructions executable by the computer to perform method steps. The method steps include computerized monitoring of effectiveness of prescribed pharmaceutical treatments in patients in conjunction with an electronic medical record and prescription compliance records. The electronic medical record contains information about a patient to receive the pharmaceutical treatment and the patient's medical history. The program instructions in the computer-readable code in the program storage device include instructions that cause a computer to perform the method steps of receiving and storing a data entry to indicate whether the patient took a pharmaceutical treatment as prescribed to form a prescription compliance record in the computer memory. The electronic medical record is then presented to a provider to enable the provider to identify trends related to a target medical parameter. Any identified trends related to the target medical parameter are then presented to the provider for analysis to note correlations in the trends with the prescription compliance record. Data entries from the provider are then stored in the electronic medical record indicating noted correlations in the trends presented. The noted correlations are then presented to the provider for analysis. Data entries from the provider's analysis indicating potential effectiveness of the pharmaceutical treatment on the target medical parameter based upon the noted correlations between the target medical parameter and the prescription compliance record are then stored in the electronic medical record.

As another embodiment of the present invention, a computerized system for monitoring potential effectiveness of a prescribed pharmaceutical treatment on a patient is advantageously provided. The system preferably includes a computer, a medication dispensation workstation, a provider analysis computer workstation, and a communications network. The computer preferably includes a computer memory that contains an electronic medical record and a prescription compliance record. The electronic medication record preferably contains information about the patient to receive prescribed pharmaceutical treatment and the patient's medical history. The prescription compliance record preferably includes information about the frequency the patient complied with prescription instructions for the pharmaceutical treatment. The medication dispensation workstation can be used to enable the prescribed pharmaceutical treatment to be dispensed and a prescription compliance record to be formed in the computer memory through the use of a data entry mechanism. The provider analysis workstation can be used to enable a provider to correlate any trends identified in the target medical parameter with the prescription compliance records. The correlations made by the provider enable the provider to evaluate potential effectiveness of the pharmaceutical treatment on the target medical parameter. The communications network can be used to electronically interconnect the medication dispensation workstation, the provider analysis workstation, and the computer to communicate with each other.

Another embodiment of the present invention includes a computer memory element stored in the computer memory containing a database. The database preferably includes data indicating a medical history of a patient and data indicating whether the patient took a pharmaceutical treatment as prescribed. The database can also include identified trends related to a target medical parameter, noted correlations in the identified trends related to the target medical parameter, potential effectiveness of the pharmaceutical treatment on the target medical parameter, identified trends related to a non-target medical parameter, noted correlations in the identified trends related to the non-target medical parameter, and potential effectiveness of the pharmaceutical treatment on the non-target medical parameter. The database can also include compliance record sorting criteria.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 6 is a pictorial representation of a computer screen used to provide operators with data relating to a medication profile of an inmate that is used to review an inmate's electronic medical record in accordance with an embodiment of the present invention;

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

As shown in FIGS. 1 through 12, exemplary embodiments of the present invention advantageously provide methods for computerized monitoring of effectiveness of pharmaceutical treatments in patients in conjunction with computerized electronic medical records stored in a computer memory 72. The electronic medical record 50 preferably contains information about a patient to receive a pharmaceutical treatment, information about the patient's medical history, and a prescription compliance record 65 containing information about a frequency in which the patient complied with prescription instructions for the pharmaceutical treatment.

Figure 3:
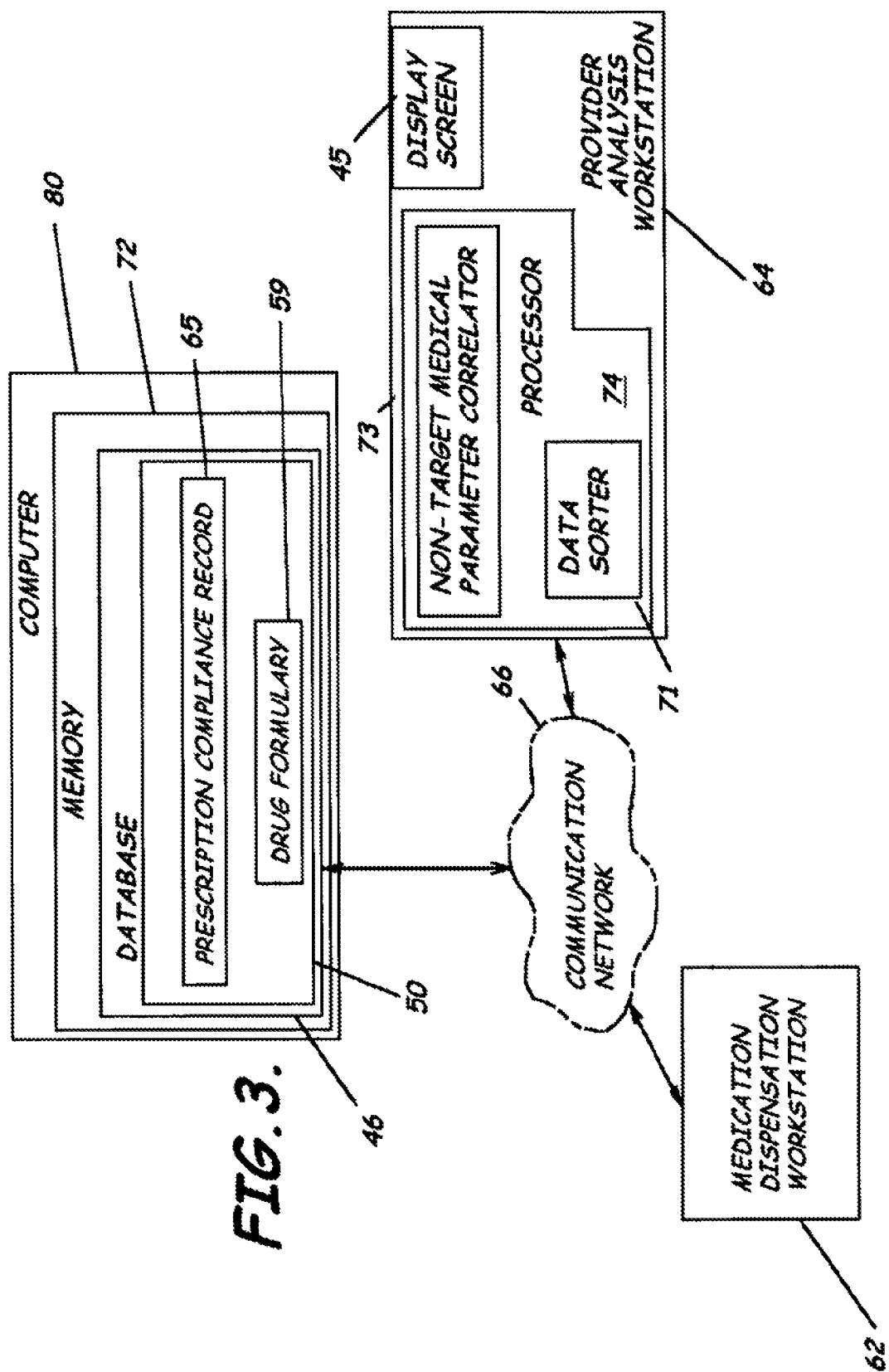
FIG. 3 is a simplified functional diagram of the components for a system for providing computerized monitoring of an effectiveness of pharmaceutical treatments for patients in accordance with an embodiment of the present invention.
Figure 4:
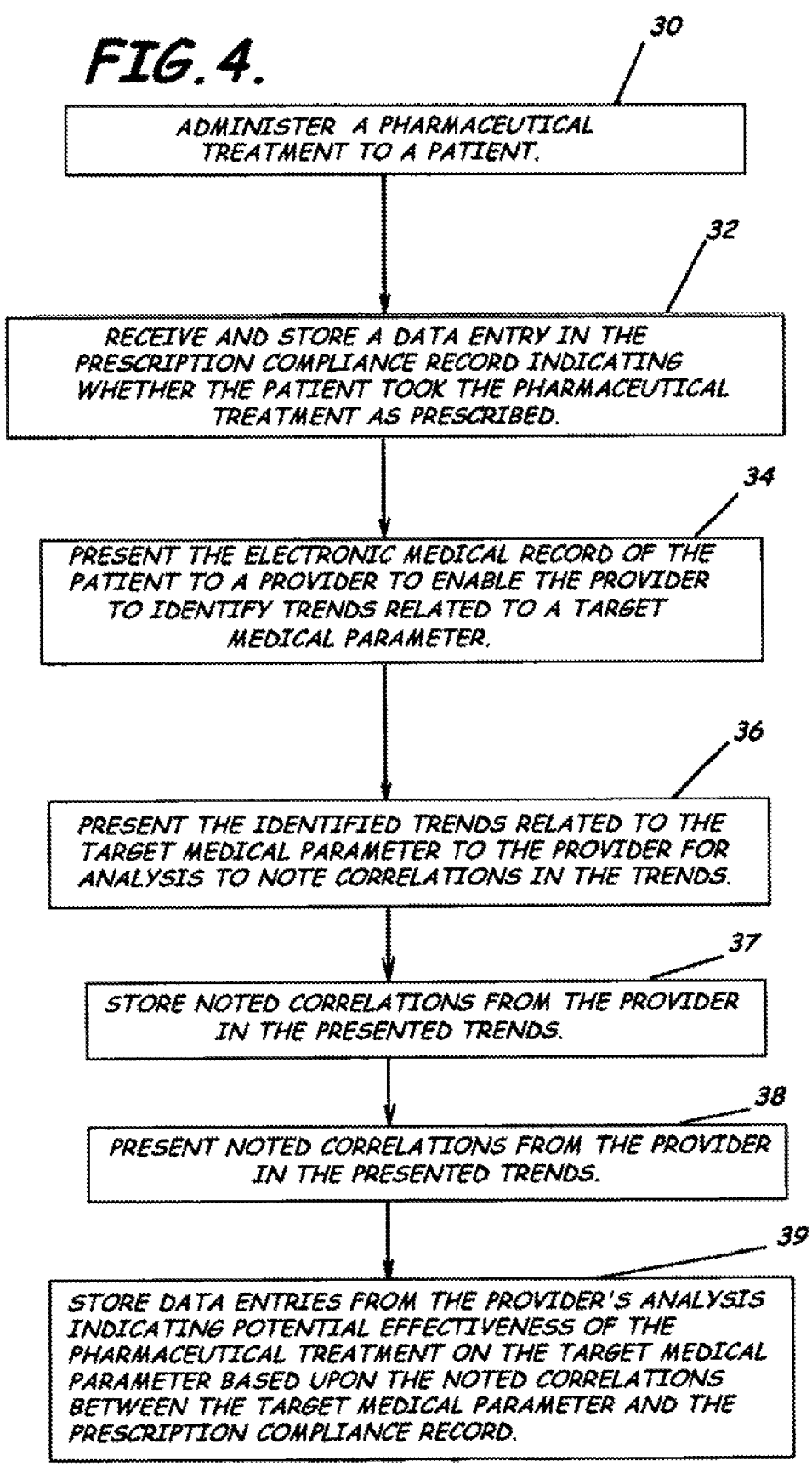
FIG. 4 is a simplified block flow diagram of a method of providing computerized monitoring of an effectiveness of pharmaceutical treatments on a target medical parameter for patients in accordance with an embodiment of the present invention.
Figure 5:
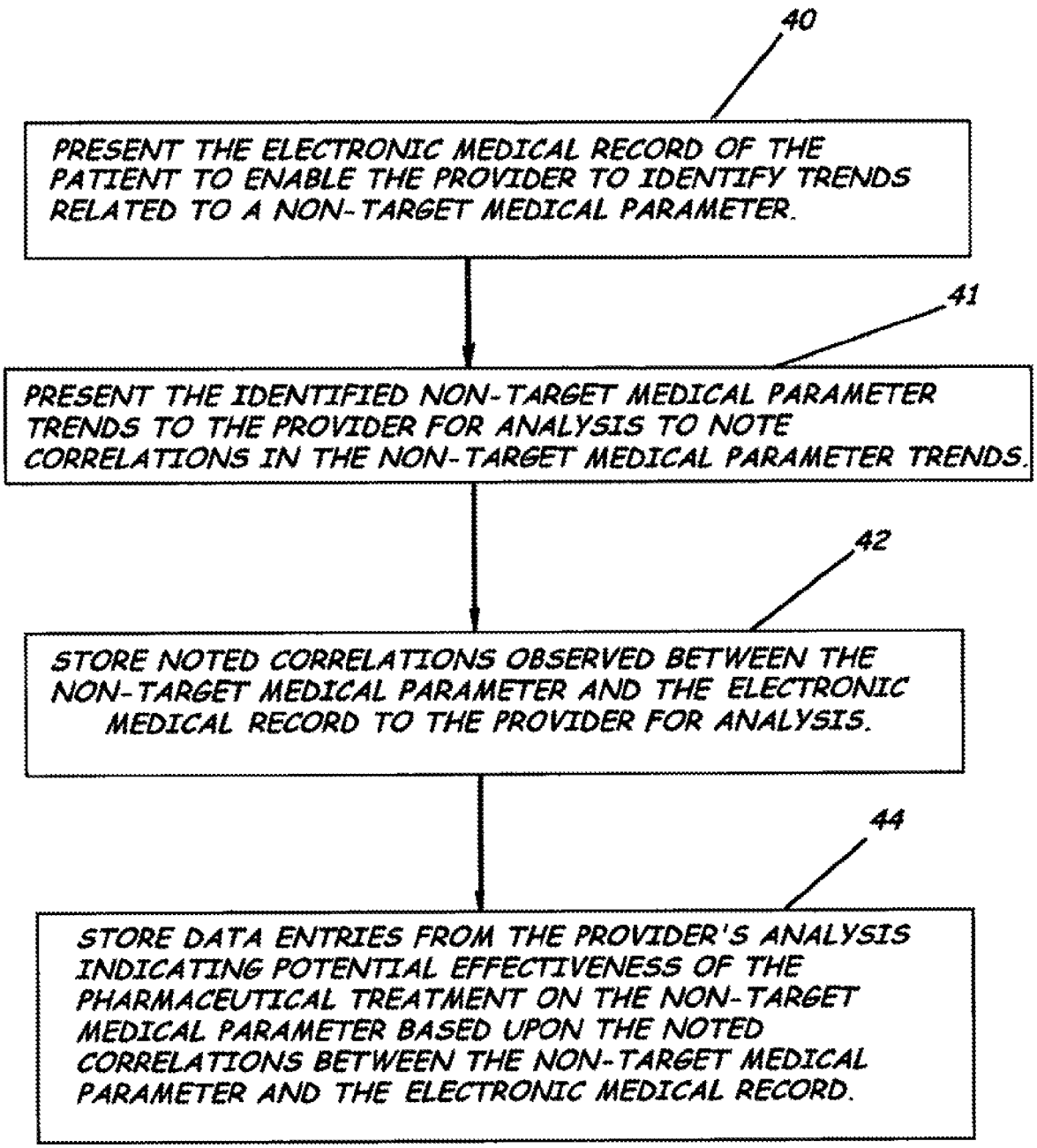
FIG. 5 is a simplified block flow diagram of a method of providing computerized monitoring of an effectiveness of pharmaceutical treatments on a non-target medical parameter for patients in accordance with an embodiment of the present invention.

As described in FIG. 4, the method or methods described herein include administering the pharmaceutical treatment to the patient, as described in step 30. This step is not performed in the computer 80, but is performed prior to any of the computerized steps described herein. The method as shown in step 32, includes the steps of receiving and storing a data entry in the prescription compliance record indicating whether the patient took a pharmaceutical treatment as prescribed to form the prescription compliance record 65 or medication administration record. The pharmaceutical treatment can be an experimental medication, an existing medication, prescription medication, over-the-counter medication, non-medicinal treatments, or combinations thereof. Combination treatments are particularly useful when dealing with patients having medical conditions, such as AIDS, that require drug "cocktails" to treat. The prescription compliance record 65 provides real-time data about the frequency in which the patient took the pharmaceutical treatment as prescribed. The prescription compliance record 65 can be a database and can be considered to be a part of the electronic medical record 50, as shown in FIG. 3. The prescription compliance record 65 allows providers to access real-time data related to the patient's medical dosing status.

The operating instructions described in the present invention are not limited to a particular computer or other server hardware, but when implemented thereon, form a special-purpose machine. Various conventional computers or servers can be used according to various embodiments of the present invention. In addition, the instructions are not described with reference to any particular programming language. It will be understood that a variety of programming languages may be used to implement the system and method of the present invention as described herein.

Figure 6:
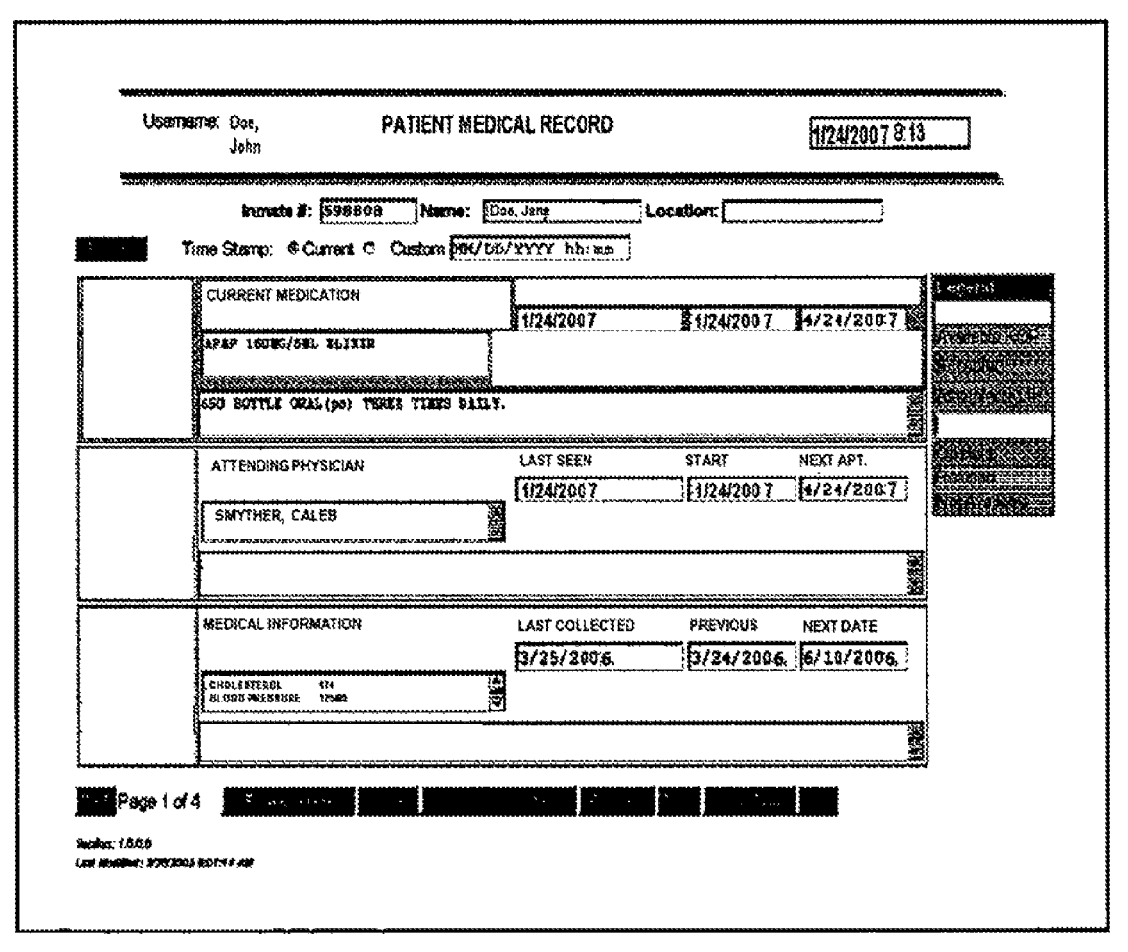

Once the prescription compliance record 65 is formed, the electronic medical record 50 is presented to a provider, as shown in step 34 of FIG. 4, to enable the provider to identify trends related to a target medical parameter. As shown in FIG. 6, the electronic medical record 50 can contain various types of information related to the patient. For example, the electronic medical record 50 preferably includes vital statistics, demographic information, lab work results, x-rays, medical checkup data, allergies, a list of current medications, and the like. Trends in non-target medical parameters can also be determined if non-target medical parameters are also affected by the pharmaceutical treatment, as described in FIG. 5.

As described in step 36 (FIG. 4), any identified trends in the target medical parameter are presented to the provider for analysis to note correlations in the trends. Noted correlations in the trends from the provider are stored in the electronic medical record 50, as described in step 37 of FIG. 4. Noted correlations from the electronic medical record 50, as described in step 38, are presented to the provider for analysis. Data entries from the provider's analysis indicating potential effectiveness of the pharmaceutical treatment on the target medical parameter, as described in step 39, based upon the noted correlations between the target medical parameter and the prescription compliance record 65 are stored in the electronic medical record 50. The effectiveness of the pharmaceutical treatment on an overall health of the patient can also be determined and evaluated, as opposed to specific parameters.

Figure 2:
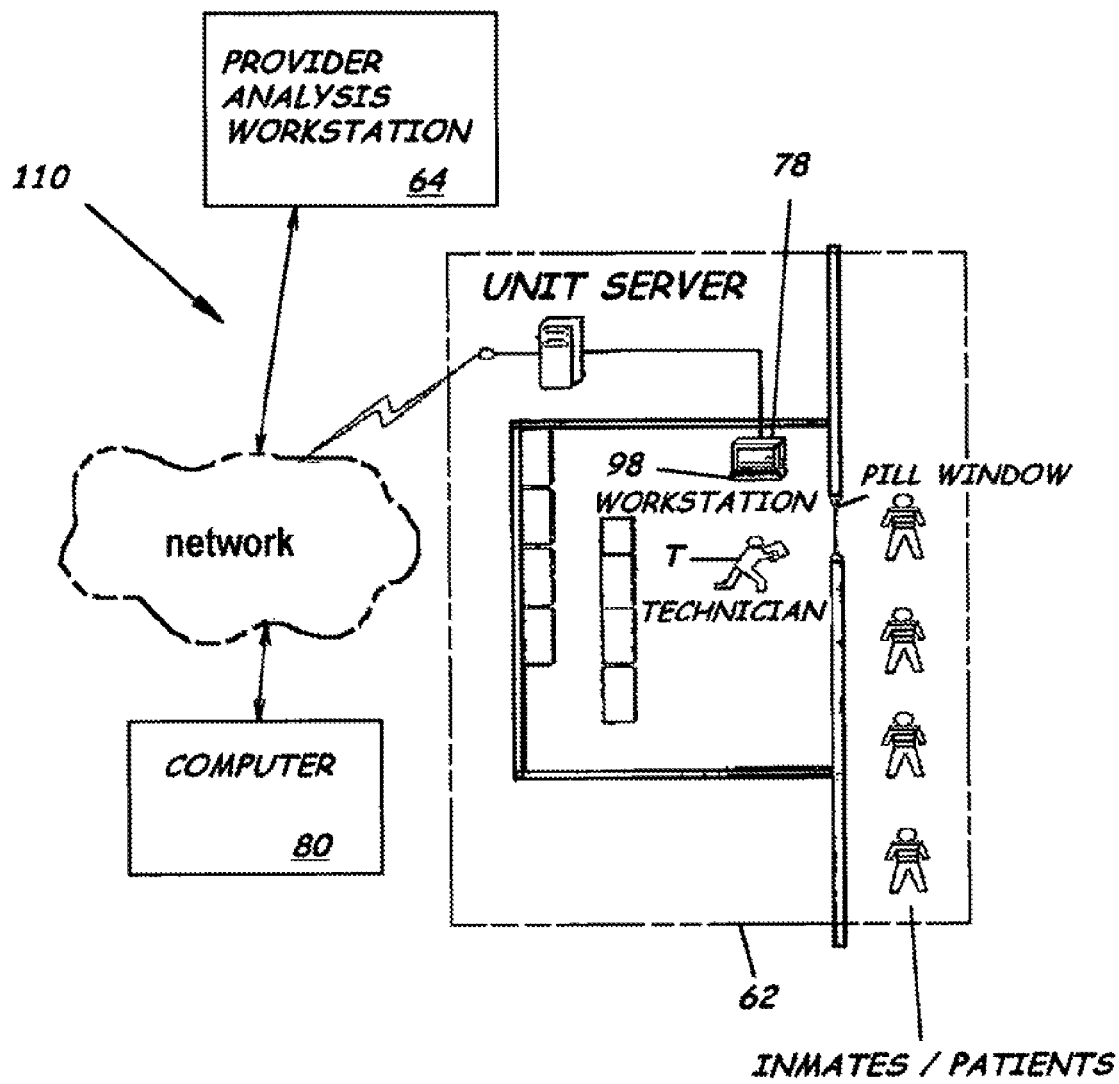
FIG. 2 is a schematic diagram of a system for computerized monitoring of dispensation of prescribed medication to patients in correctional facilities in accordance with an embodiment of the present invention.

The methods, program code, program devices, and systems described herein can be, but are not required to be, used in correctional facilities where the use of pharmaceutical treatments is monitored closely. For example, the location (FIG. 2) from which pharmaceutical treatments are administered in correctional facilities is often called a "pill window." As shown in FIG. 2, at the pill window or medication dispensation workstation 62, a prescription compliance record 65 is formed in the computer 80 verifying the dispensation of the pharmaceutical treatment to the inmate, the receipt of the pharmaceutical treatment by the patient, and verifying that the patient took the pharmaceutical treatment. This prescription compliance record 65 can be used to provide verification reports to evidence that the correctional facility at least attempted to provide medical services for the patient. The resulting prescription compliance record 65 provides real-time records that show the frequency that the patient or inmate took the pharmaceutical treatment.

In one or more preferred embodiments of the present invention, the step of making data entries to indicate whether a patient took a pharmaceutical treatment as prescribed to form a prescription compliance record 65 includes confirming whether the patient took the pharmaceutical treatment as prescribed. The formation of the prescription compliance record 65 preferably occurs contemporaneously, i.e., at approximately the same time, to the patient taking the pharmaceutical treatment. By forming the prescription compliance record 65 contemporaneously to the patient taking the pharmaceutical treatment, the prescription compliance record 65 contains real-time data that is accurate and up-to-date.

Various embodiments of the present invention permit the provider to determine the effectiveness of the pharmaceutical treatment on a target medical condition or ailment. The systems, program code, program devices, and methods described herein preferably allow the provider to perform drug utilization reviews to determine the appropriateness of the pharmaceutical treatment utilizing real time, compliance data related to the patient. In order to do this, the step of presenting noted correlations from the electronic medical record 50 includes presenting noted correlations of a plurality of patients having the target medical condition to the provider for analysis to identify trends related to the target medical parameter. For example, noted correlations from the electronic medical record 50 can be presented to the provider for a patient having the target medical condition, such as diabetes, to determine the effect of the pharmaceutical treatment on medical parameters typically associated with patients having diabetes. Data entries from the provider indicating trends related to the target medical parameter on the plurality of patients are stored in the electronic medical record 50. The noted correlations from the electronic medical record 50 are presented to the provider for analysis. Once the provider has analyzed the data, data entries are stored indicating the trends related to the target medical parameter of the plurality of patients having the target medical condition to determine the potential effectiveness of the pharmaceutical treatment on the plurality of patients having the target medical condition.

Figure 8:
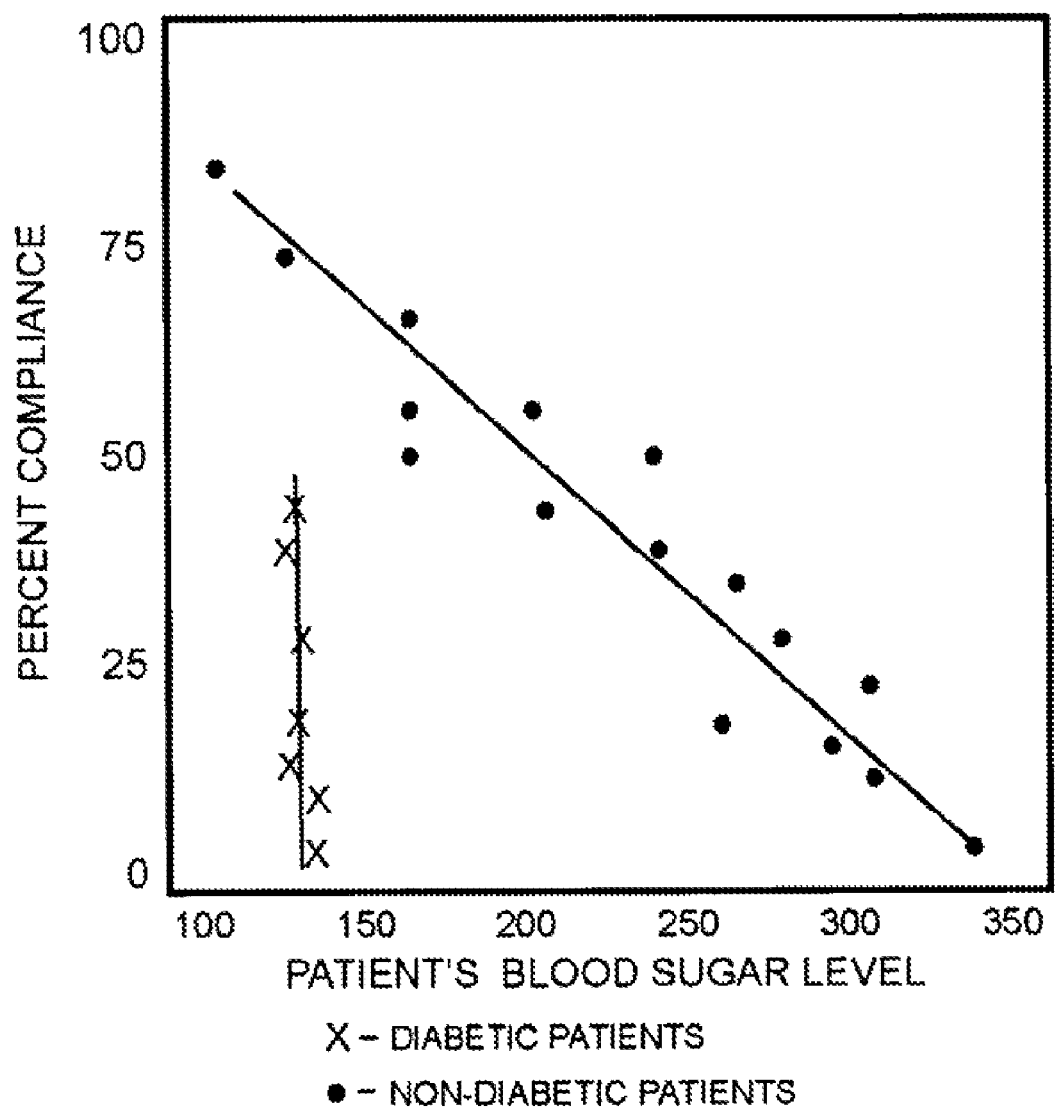
FIG. 8 is a pictorial representation of an example computer screen display in accordance with an embodiment of the present invention used to provide operators with data correlating a patient's blood sugar level medical parameter with the patient's prescription compliance record both for patients having a diabetic medical condition and for patients that do not have a diabetic medical condition.
Figure 9:
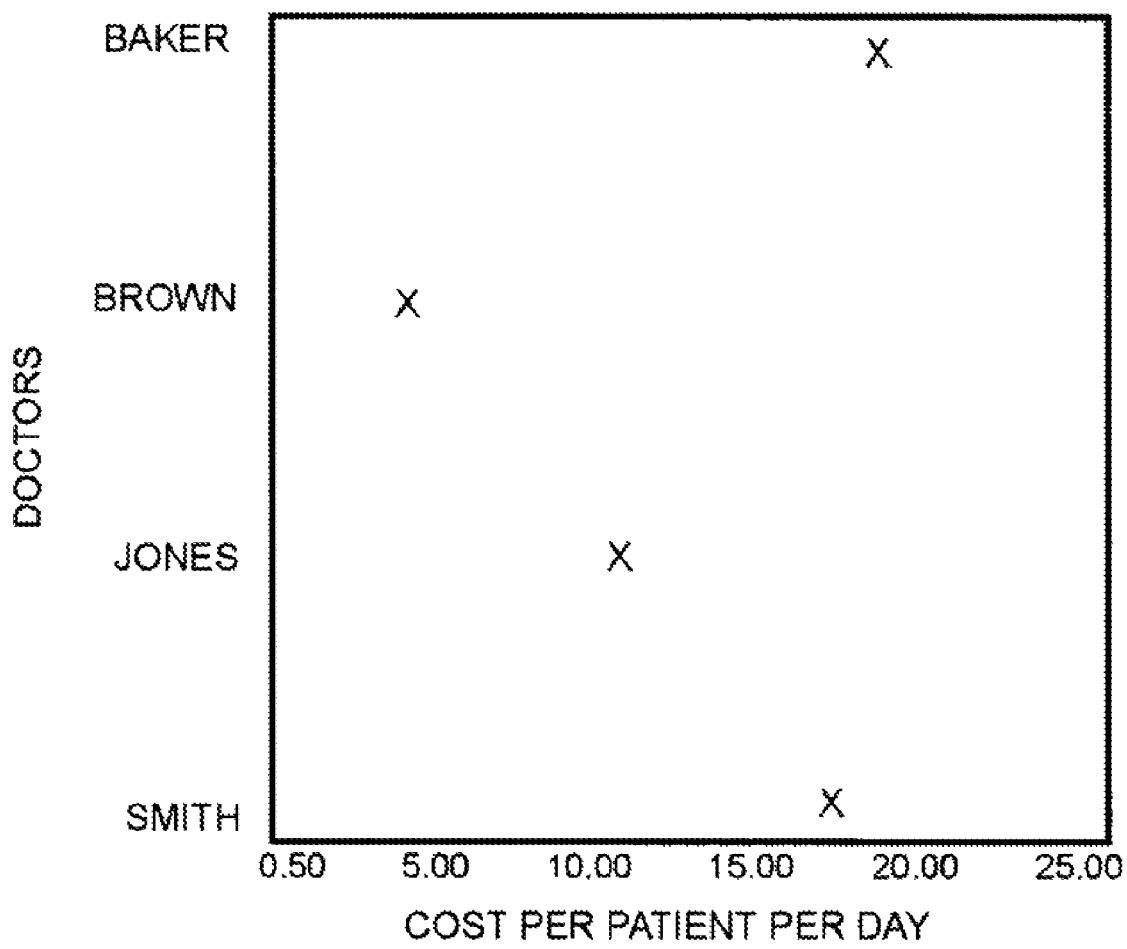
FIG. 9 is a pictorial representation of an example computer screen display in accordance with an embodiment of the present invention used to provide operators with data relating to comparing the prescription costs per day associated with different providers.

In order to determine the effectiveness of the pharmaceutical treatment on a large population, the identified trends related to the target medical parameter of each patient having the target medical condition can be compared with other patients having the same target medical condition. This is done to determine the effectiveness of the pharmaceutical treatment on a group of patients having the target medical condition, as shown in FIG. 8. For example, the target medical parameter of fasting blood sugar level can be compared for patients having the target medical condition of diabetes and also for those patients that do not have diabetes. With a large population of patients, multiple target medical conditions can also be evaluated. For example, the effectiveness of a pharmaceutical treatment can be evaluated for patients having diabetes and also high blood pressure as another target medical condition.

To further enable providers to efficiently determine the effectiveness of the pharmaceutical treatment on the medical condition, the correlations determined between the trends and the prescription compliance record 65 can be sorted as a basis for further analysis. This can take the form, for example, of sorting by criteria, such as prescription level (i.e., one pill per day), compliance level (i.e., the patient took the pharmaceutical treatment as prescribed 95% of the time), medical condition (i.e., diabetes), medical parameter (i.e., red blood cell count), provider (i.e., physician), prescription costs (i.e., costs for pharmaceutical treatment for the patient), patient demographics (i.e., 40 years old), and combinations thereof. Other desirable sorting criteria will be apparent to those of skill in the art and are to be considered within the scope of the present invention.

Figure 7:
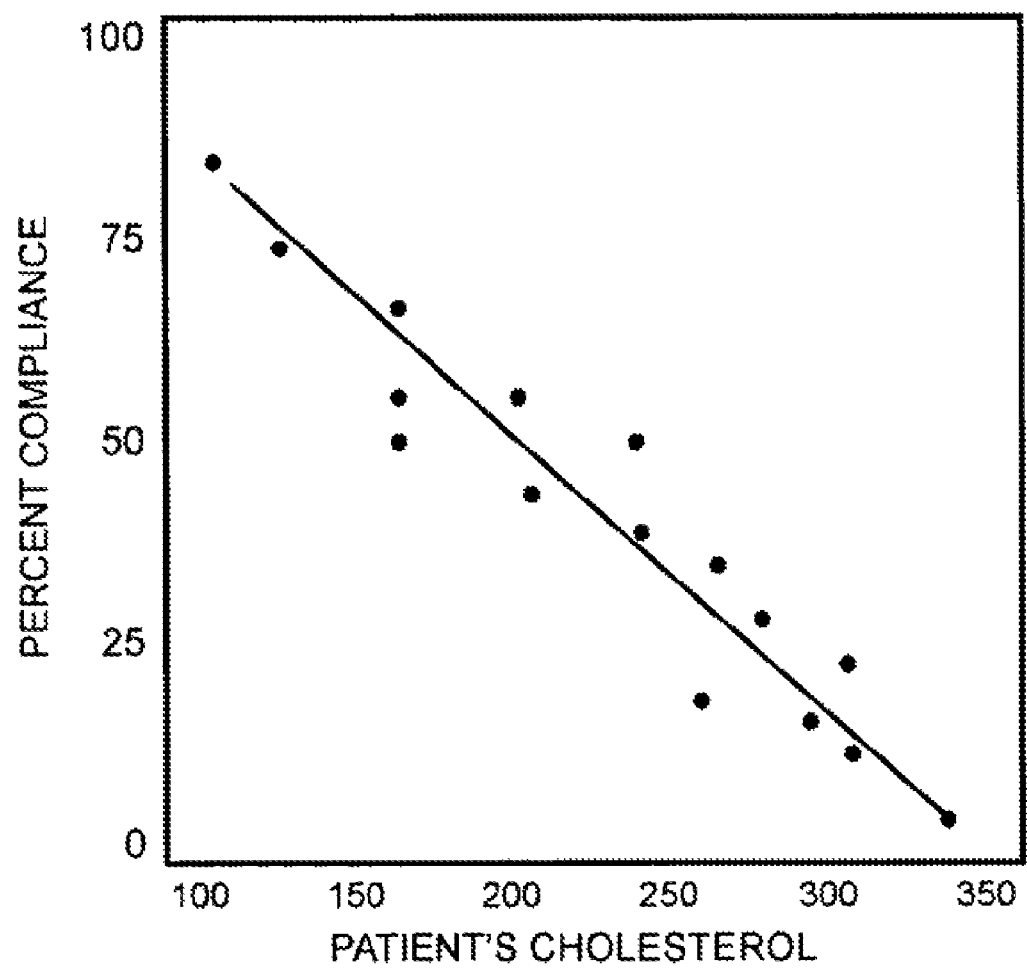
FIG. 7 is a pictorial representation of an example computer screen display in accordance with an embodiment of the present invention used to provide operators with data correlating a patient's cholesterol medical parameter with the patient's prescription compliance record.

Different compliance levels can affect the effectiveness of the pharmaceutical treatment on both target and non-target medical parameters, as shown in FIGS. 7 and 8. For example, if a patient took their blood pressure medication 100% of the time, the blood pressure medication reduced their cholesterol by 20%. However, if the patient only took the blood pressure medication 60% of the time, then they experienced severe headaches and their cholesterol level did not improve. In this example, if the patient complied and took blood pressure medication 100% of the time, the pharmaceutical treatment was beneficial. If the patient only complied 60% of the time, not only did the pharmaceutical treatment not work, but the patient also experienced detrimental side effects. The patient would have been better off not taking the pharmaceutical treatment at all than only 60% of the time. In order to evaluate this type of behavior, the step of determining an effectiveness of the pharmaceutical treatment on the target medical parameter preferably includes determining the effectiveness of the pharmaceutical treatment on the target medical parameter at different compliance levels with constant prescription levels, as shown in FIGS. 7 and 8. This feature enables providers to determine an optimal prescription level for the pharmaceutical treatment.

Figure 10:
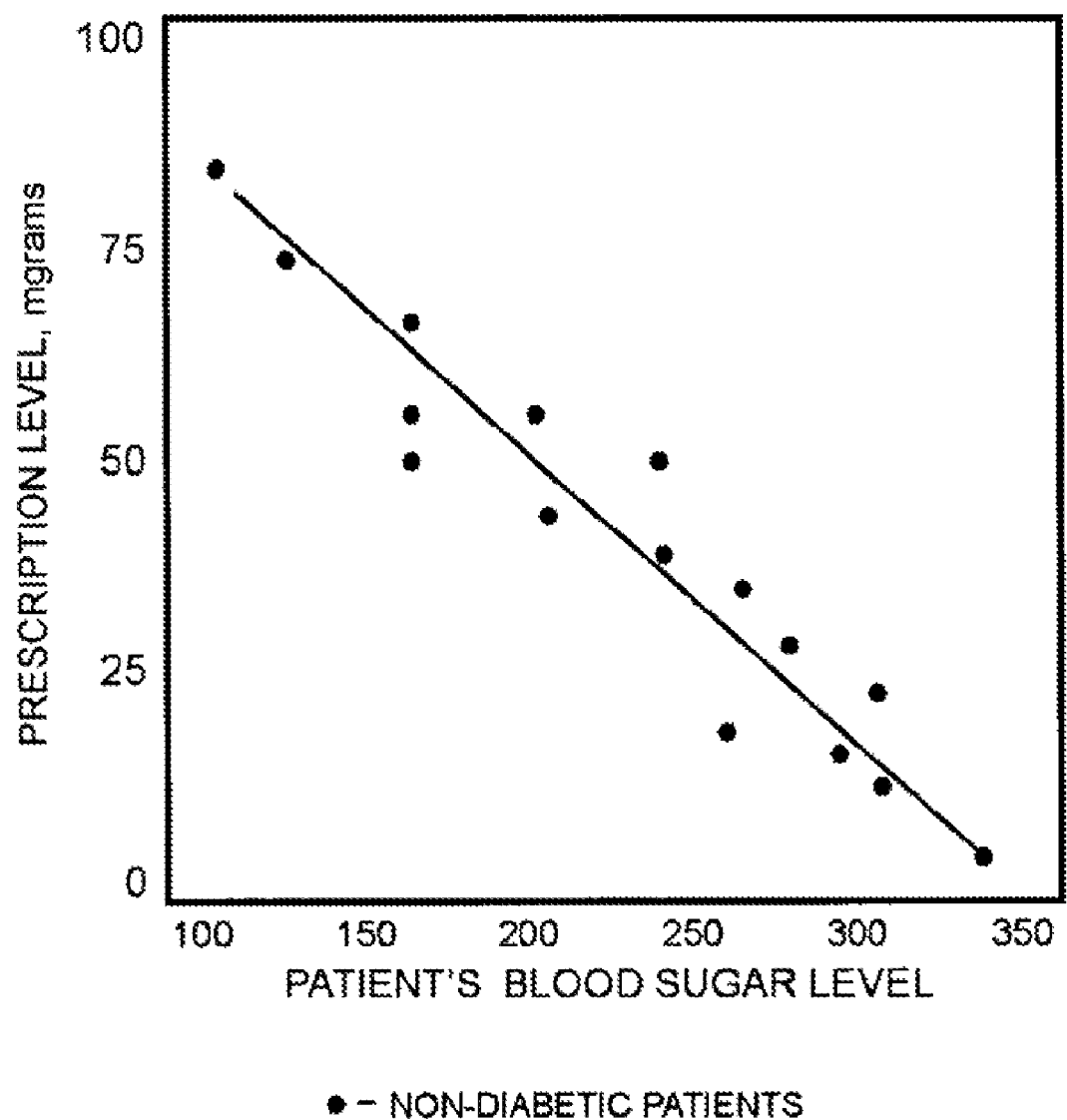
FIG. 10 is a pictorial representation of an example computer screen display in accordance with an embodiment of the present invention used to provide operators with data correlating a patient's blood sugar level medical parameter with the patient's prescription medication level.

Similarly, the amount of the pharmaceutical treatment can also affect the effectiveness of the pharmaceutical treatment. For example, 500 milligrams of a pain reliever can be beneficial to a healthy patient to relieve a headache when the patient takes the pain reliever 100% of the time as prescribed. However, a very large dosage, such as 5000 milligrams, of the pain reliever can make the patient sick to their stomach if they take the pain reliever 100% of the time as prescribed. In order to evaluate whether the amount of pharmaceutical prescribed is a pharmaceutically effective amount, the step of determining an effectiveness of the pharmaceutical treatment on the target medical parameter preferably includes determining the effectiveness of the pharmaceutical treatment on the target medical parameter at different prescription levels with constant compliance levels, as shown in FIG. 10.

Figure 11:
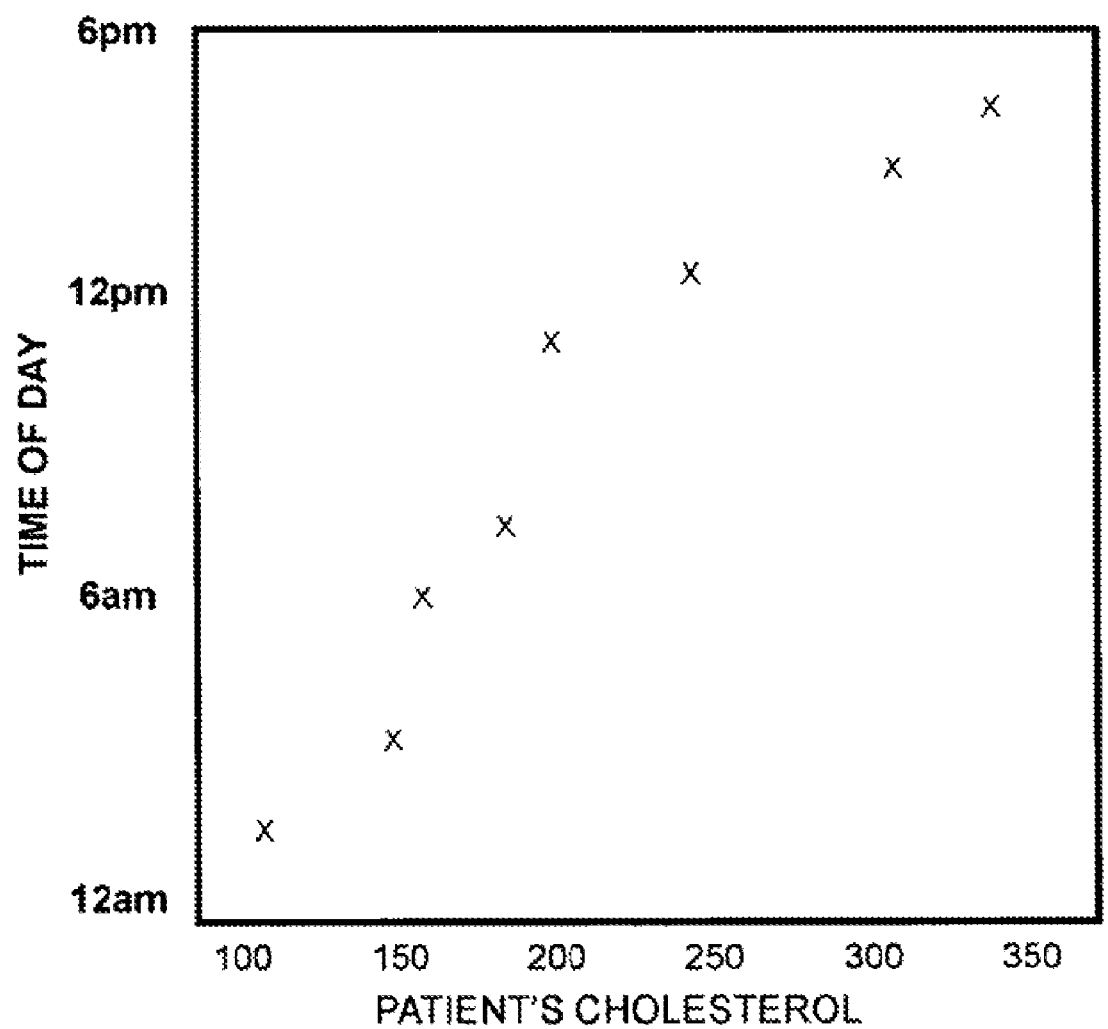
FIG. 11 is a pictorial representation of an example computer screen display in accordance with an embodiment of the present invention used to provide operators with data correlating a patient's cholesterol medical parameter with the patient's dispensation time.

The time of day that the pharmaceutical treatment is dispensed to the patient may affect its performance on the patient's medical parameter. To determine the effect of the dispensation time on the performance of the pharmaceutical treatment, embodiments of the present invention preferably include the step of determining the effectiveness of the pharmaceutical treatment on the target medical parameter at various pharmaceutical treatment dispensation times, as shown in FIG. 11. When making the evaluation of effect of the dispensation time of the pharmaceutical treatment on the medical parameter, the prescription level and compliance levels are preferably kept constant.

Figure 12:
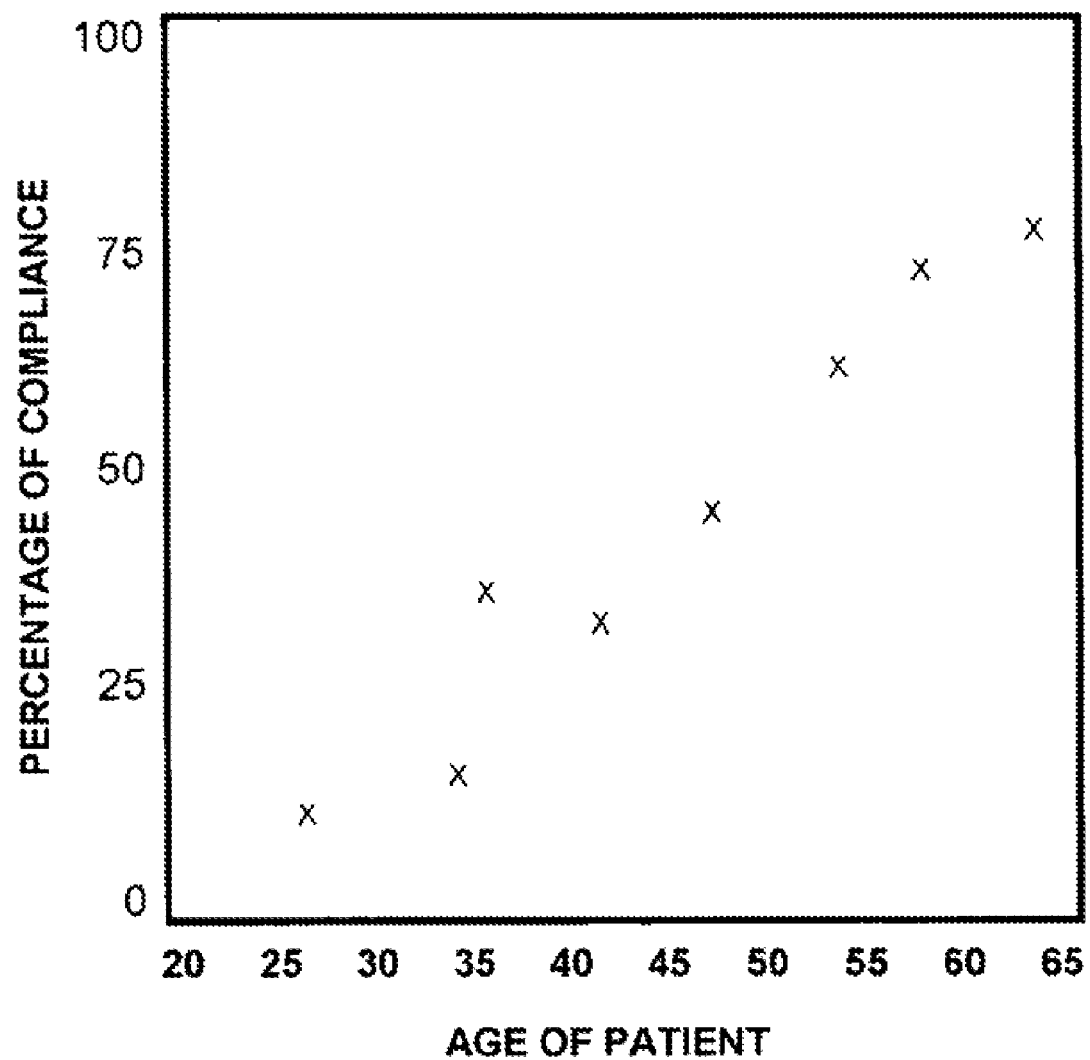
FIG. 12 is a pictorial representation of an example computer screen display in accordance with an embodiment of the present invention used to provide operators with data correlating a patient's cholesterol medical parameter with the patient's age.

Demographic factors of the patient can also affect the effectiveness of the pharmaceutical treatment on the target medical parameter, as can be seen in FIG. 12. Demographic factors that may affect how the target and non-target medical parameters respond to the pharmaceutical treatment can include age, ethnicity, gender, weight, and the like. To evaluate the effectiveness of the pharmaceutical treatment on medical parameters on patients with different demographic factors, embodiments of the present invention preferably include the step of determining the effectiveness of the pharmaceutical treatment for various demographic factors. When evaluating the effect of the demographics on the medical parameter, the prescription level and compliance level are preferably kept constant.

In addition to the target medical parameter, other non-target medical parameters can be affected as a result of the pharmaceutical treatment on the patient. For example, if a patient with a diabetic medical condition is given a pharmaceutical treatment to lower their fasting blood sugar level, the pharmaceutical treatment could also affect another non-target medical parameter, such as their blood pressure. In order to evaluate this type of occurrence, the methods described herein preferably include a step 40 (FIG. 5) of presenting the electronic medical record 50 of the patient to enable the provider to identify trends related to a non-target medical parameter. The identified non-target parameter trends related to the non-target medical parameter can then be presented to the provider for analysis as indicated at step 41 to note correlations in the non-target medical parameter trends in the computer memory 72. Based upon the correlations obtained during step 41, the noted correlations from the provider in the non-target medical parameter trends are stored in the computer memory 72. The noted correlations observed between the non-target medical parameter and the prescription compliance record 65 are presented to the provider for analysis. After the provider has analyzed the noted correlations between the non-target medical parameter and the prescription compliance record 65, data entries are stored indicating potential effectiveness of the pharmaceutical treatment on the non-target medical parameter, as described in step 44, based upon the presented noted correlations between the non-target medical parameter and the prescription compliance record 65.

To assist providers in providing the best health care possible at the lowest price, the methods, program code, program devices and systems according to various embodiments of the present invention can also be used to assess the pharmaceutical treatments that should be included in a drug formulary 59 in institutes. Drug formularies 59 are typically used in facilities such as correctional facilities, military facilities, and hospitals. Drug formulary 59 is a schedule of pharmaceutical treatments that are approved for use that can be used and dispensed through the facility and its associated pharmacy. Based upon the results of the determination of the effectiveness of pharmaceutical treatments, the drug formulary 59 for institutes can be updated with either additions or deletions based upon the evaluations and techniques of the present invention. The drug formulary 59 preferably is continuously maintained thereby making the drug formulary 59 a real-time database that includes a readily available list of drugs.

Exemplary methods described herein can include the step of modifying the drug formulary 59 based upon the effectiveness of the pharmaceutical treatment. When generic medication enters the marketplace, providers are somewhat hesitant to modify the patient's prescription because the provider knows the effect of the current medication. If substitute medications can be evaluated, then drug formularies can be modified or updated to include the results of the determination of the effectiveness of the substitute pharmaceutical treatment. For example, if a generic brand of ibuprofen has been shown to be as effective or more effective than a name brand, more expensive, version of ibuprofen, then the lower priced ibuprofen can be added to the drug formulary 59 as a suitable substitute or replacement pharmaceutical treatment.

Various embodiments of the present invention advantageously provides a program storage device 57 readable by a computer 80, tangibly embodying a computer-readable code of program instructions executable by the computer 80 to perform method steps. The method steps include computerized monitoring of effectiveness of prescribed pharmaceutical treatments in patients in conjunction with the electronic medical record 50. Specifically, the method steps of the program instructions in the computer-readable code in the program storage device include the method steps of receiving and storing the data entry during step 32 of FIG. 4 to indicate whether a patient took a pharmaceutical treatment as prescribed. The data entry forms a prescription compliance record 65 in the computer memory 72. An electronic medical record 50 of the patient is then presented during step 34 to the provider to enable the provider to identify trends related to a target medical parameter. Any identified trends related to the target medical parameter are presented in step 36 to the provider for analysis to note correlations in the trends. Noted correlations from the provider in the presented trends are then stored, as described in step 37, in the computer memory 72. Noted correlations from the provider in the presented trends are then presented to the provider for analysis, as described in step 38. Data entries from the provider's analysis indicating potential effectiveness of the pharmaceutical treatment on the target medical parameter based upon the noted correlations observed between the target medical parameter and the prescription compliance record 65 are stored in the computer memory 72, as described in step 39.

Figure 1:
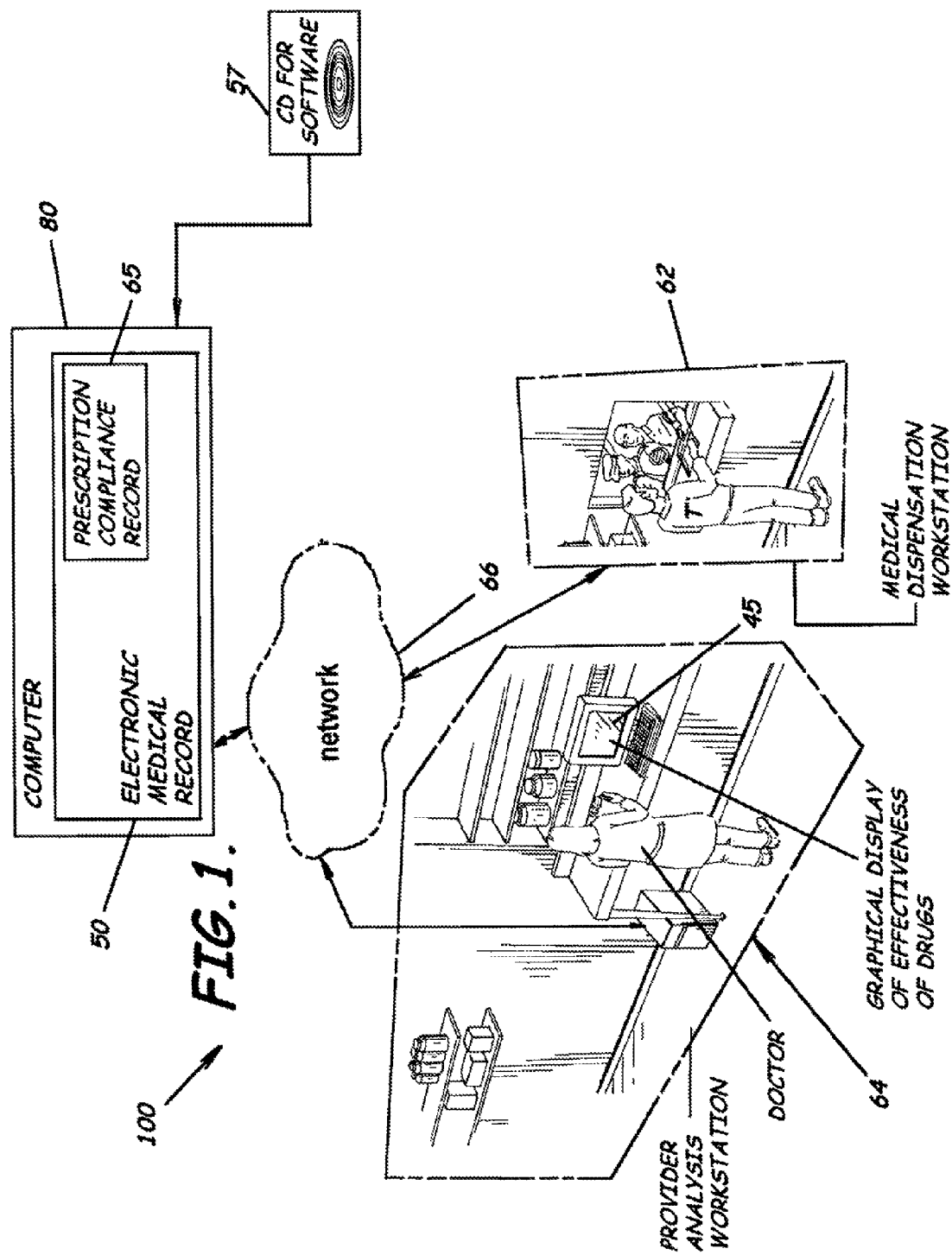
FIG. 1 is a schematic diagram of a system for computerized monitoring of an effectiveness of pharmaceutical treatments for patients in accordance with an embodiment of the present invention.

Various embodiments of the present invention also provides a computerized system for monitoring effectiveness of the prescribed pharmaceutical treatment on the patient in conjunction with the electronic medical record 50 stored in computer memory 72, as shown in FIGS. 1 and 3. The system preferably includes a computer 80, a medication dispensation workstation 62, a provider analysis workstation 64, and a communications network 66. According to an exemplary embodiment, the computer 80 includes a computer memory 72 that contains the electronic medical record 50 and the prescription compliance record 65. The electronic medical record 50 contains information about the patient to receive prescribed pharmaceutical treatment and the patient's medical history. The prescription compliance record 65 includes information about the frequency the patient complied with prescription instructions for the pharmaceutical treatment. The computer memory 72 also includes software and programs that enable the computer 80 to operate and communicate with the network 66. For example, the computer memory 72 preferably includes operating and display programs and communications and networking server software.

The medication dispensation workstation 62 can be used to enable the prescribed pharmaceutical treatment to be dispensed and a prescription compliance record 65 to be formed or created in the computer memory 72. Medicinal administration within confinement facilities, such as prisons, has been different than medicinal administration for the general public. Medicinal administration within prisons has been a hybrid type of system because a portion of the administration is done on an outpatient type of basis, similar to that experienced by the general public, and a portion of it is similar to having medicine administered in an inpatient type setting, such as experienced by patients in the hospital. Medicinal administration within prisons has aspects that are similar to medicinal administration within nursing homes. For example, the general public receives a prescription from a doctor and a pharmacy fills the prescription. The individual typically obtains a bottle with the entire amount of prescribed medication contained within the bottle. The bottle typically contains instructions for ingesting the medication, such as the duration in which the individual needs to ingest the medication. No one verifies that the individual took the prescribed medication, as suggested by the provider. In the correctional facilities and sometimes nursing homes, the medication is individually packaged in single serving dosage packs, or blister packs. The prison system and nursing homes keep custody of prescribed medication until administered. The single dose is then administered to the patient and, in correctional facilities, a guard typically verifies that the medication has been taken.

In correctional facilities, the location from which pharmaceutical treatments are administered in correctional facilities is often called a "pill window." Pill windows or medication dispensation workstation 62 at correctional facilities are operated by technicians that dispense pharmaceuticals to inmates, including both prescribed medication and over-the-counter medication. The pill window technician can review medical data related to the inmate prior to dispensation of the medication to the inmate. For example, the pill window technician can review information about the inmate related to a list of active medications for a patient, a medical profile for the inmate, the medical compliance for the patient's prior prescriptions, and patient allergy information.

In addition to reviewing data, the pill window technician has the ability to record the administration of a prescription to a patient, to record administration of medication from floor stock, and to document medication errors, and to record medication waste through the use of a data entry mechanism 98, as shown in FIG. 2. The electronic medical record 50 contains information about a target medical parameter of the patient. The provider analysis workstation 64 is used to enable a provider to correlate any trends in the target medical parameter with the prescription compliance records 65.

As used herein, the term provider can be anyone who provides medical care to a patient. Examples include a discharge nurse, a medical specialist, a physician, a nurse assistant, a nurse, a physician advisor, and a radiologist. Technicians, as used herein, are people that provide support functions for the providers. Examples include sample technicians, lab technicians, and radiology technicians. Other types of providers and technicians will be apparent to those of ordinary skill in the art and are to be considered within the scope of the present invention.

The provider analysis workstation 64 enables the provider to correlate any trends identified in the target medical parameter with the prescription compliance record to determine potential effectiveness of the pharmaceutical treatment on the target medical parameter. The provider analysis workstation 64 contained within the computerized system of the present invention preferably also includes a display screen 45 to graphically display the correlations determined between the identified trends and the prescription compliance record 65. The display screen 45 will enable the provider to easily observe correlations in the identified trends for both target and non-target medical parameters and the prescription compliance record 65.

The provider analysis workstation 64 also preferably includes a processor 74 that contains a data sorter 71 that is capable of sorting the correlations determined between the trends and the prescription compliance record 65 by sorting criteria selected from the group consisting of prescription level, compliance level, medical condition, medical parameter, provider, prescription costs, patient demographics, and combinations thereof. Other suitable sorting criteria will be apparent to those of ordinary skill in the art and are to be considered within the scope of the present invention.

The processor 74 preferably contains a non-target medical parameter correlator 73 to enable providers to correlate any identified trends in a non-target medical parameter with the prescription compliance record 65. The non-target medical parameter correlator 73 enables the provider to determine the effect, if any, of the pharmaceutical treatment on non-target medical parameters, in addition to the correlations determined between the target medical parameter and the prescription compliance record 65.

The communications network 66 electronically interconnects the medication dispensation workstation 62, the provider analysis workstation 64, and the computer 80 to communicate with each other. The electronic medical record 50 and the prescription compliance records 65 are stored in the computer memory 72.

The computerized system of the present invention preferably also includes a drug formulary 59 that can be updated based upon the effectiveness of the pharmaceutical treatment on the target medical parameter. As described herein, if the effectiveness of a less expensive pharmaceutical treatment is the same or greater than a more expensive pharmaceutical treatment that is currently on the formulary, the formulary can be modified to include the less expensive pharmaceutical treatment. This feature enables facilities to ensure that they are using the most effective pharmaceutical treatment for the money.

Another embodiment of the present invention provides a computer memory element stored in the computer memory 78 (tangible computer readable medium) containing a database 46 or a set or grouping of databases containing data in computer-readable format, as shown in FIG. 3. The database 46 is preferably stored in the computer memory 78 or in other suitable data storage media accessible to the computer 80. The database 46 can also be provided in the form of a database server or server cluster. The particular database configuration is replicated based on capacity requirements for the system. The database 46 preferably includes data indicating a medical history of the patient and data indicating whether the patient took a pharmaceutical treatment as prescribed. The data indicating the medical history of the patient preferably includes the electronic medical record 50, as described herein. The data indicating whether the patient took the pharmaceutical treatment as prescribed preferably includes the prescription compliance record 65.

In preferred embodiments of the present invention, the database 46 also includes data indicating identified trends related to the target medical parameter. The data indicating identified trends related to the target medical parameter are based upon analysis made by the provider indicating that the target medical parameter was affected by the consumption of the pharmaceutical treatment by the patient, which was confirmed in the prescription compliance record 65. The database 46 can also include data indicating noted correlations in the identified trends related to the target medical parameter. The provider analyzes the data indicating noted correlations in the identified trends related to the target medical parameter to determine the potential effectiveness of the pharmaceutical treatment on the target medical parameter. The database 46 can also include data indicating potential effectiveness of the pharmaceutical treatment on the target medial parameter based upon the noted correlations between the target medical parameter and the prescription compliance record.

In preferred embodiments of the present invention, the database 46 includes data indicating compliance record sorting criteria. The sorting criteria include prescription level, compliance level, medical condition, medical parameter, provider, prescription costs, patient demographics, and combinations thereof. In preferred embodiments of the present invention, the database 46 also preferably includes data indicating potential effectiveness of the pharmaceutical treatment on the target medical parameter at various compliance levels, various prescription levels, various prescription costs, various pharmaceutical treatment dispensation times, and various demographic factors.

Possible variations can include different compliance levels with constant prescription levels, different prescription levels with constant compliance levels, different prescription costs associated therewith constant prescription and compliance levels, different pharmaceutical treatment dispensation times with constant prescription and compliance levels, and different demographic factors with constant prescription and compliance levels. Other variations will be apparent to those of ordinary skill in the art and are to be considered within the scope of the present invention.

In addition to data related to the target medical parameter, the database 46 can also include data related to the non-target medical parameter. If the pharmaceutical treatment affects the non-target medical parameter, then this information can also be stored in the database 46. The database 46 can include data indicating identified non-target medical parameter trends related to the non-target medical parameter indicating correlations in the non-target medical parameter trends. The database 46 can include data indicating noted correlations in the identified non-target medical parameter trends. The database 46 can also include data indicating potential effectiveness of the pharmaceutical treatment on the non-target medical parameter.

As described herein, the database 46 preferably includes the drug formulary 59, as shown in FIG. 3. The drug formulary 59 can be updated based upon the effectiveness of pharmaceutical treatments on patients.

An advantage of various embodiments of the present invention is that health care providers are able to provide better care to patients. The objective data that is collected about a patient enables providers to determine the effectiveness of the pharmaceutical treatment that they have prescribed. As another advantage of various embodiments of the present invention, drug companies preferably utilize a larger population of patients having a target medical condition and monitor both target medical parameters and non-target medical parameters. The prescription compliance records 65 will also enable clinical study administrators to review objective imperial data regarding the effect of pharmaceutical treatments on patients. Clinical study administrators do not have to hope that the study subjects have been truthful or accurate regarding the frequency in which they complied with their prescribed pharmaceutical treatment. This feature increases the accuracy of the clinical studies, as well.

As another advantage, various embodiments of the present invention can be integrated with telemedicine programs to allow providers to access data about patients all over the world. The systems, program code, program devices, and methods described herein can be used in foreign countries that have access to pharmaceutical treatments not currently available in the United States. Pharmaceutical treatment knowledge can be shared globally to allow providers in remote locations to access data regarding the effectiveness of pharmaceutical treatments.

This application is related to U.S. patent application Ser. No. 10/959,627 filed Oct. 6, 2004, titled "Pharmaceutical Treatment Effectiveness Analysis Computer System and Methods," which is a continuation-in-part of U.S. patent application Ser. No. 10/806,878, filed on Mar. 23, 2004, titled "Pharmaceutical Inventory and Dispensation Computer System and Methods," each incorporated by reference in its entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

That claimed is:

1. A method for computerized monitoring of effectiveness of pharmaceutical treatments under evaluation in patients, the method comprising the steps of:

receiving by a computer, data for each of a plurality of patients indicating whether the respective patient self-administered a pharmaceutical treatment under evaluation as prescribed to thereby document patient compliance with prescription instructions for the pharmaceutical treatment under evaluation; and responsive to the received data, determining a potential effectiveness of the pharmaceutical treatment under evaluation on a target medical parameter, the step of determining a potential effectiveness of the pharmaceutical treatment under evaluation on the target medical parameter including the steps of:

analyzing a trend related to the target medical parameter indicating effects of consumption of the pharmaceutical treatment under evaluation by the plurality of patients at a plurality of different pharmaceutical treatment compliance levels at each of one or more constant prescription levels to thereby determine a correlation, when existing, between the trend related to the target medical parameter and compliance level associated with the respective one or more constant prescription levels for the pharmaceutical treatment under evaluation, responsive to the step of analyzing, determining an effect of compliance level on effectiveness of the pharmaceutical treatment under evaluation at each of the one or more constant prescription levels, and responsive to the step of determining an effect of compliance level, determining a threshold level of compliance for each of the one or more constant prescription levels below which receiving the pharmaceutical treatment under evaluation at the respective prescription level results in an effect that is less desirable than an effect of not receiving the pharmaceutical treatment under evaluation.

2. The method as defined in claim 1, wherein the step of determining the potential effectiveness of the pharmaceutical treatment under evaluation on the target medical parameter comprises the step of:
   determining for each of the one or more constant prescription levels, a minimum level of compliance necessary to have a positive effect on the target medical parameter exceeding that of not receiving the pharmaceutical treatment under evaluation.

3. The method as defined in claim 1,
   wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter at each of the plurality of different compliance levels at constant prescription level for each of a plurality of different prescription levels; and
   wherein the step of determining an effect of compliance level on effectiveness of the pharmaceutical treatment under evaluation at each of the one or more constant prescription levels includes determining an effect of compliance level on effectiveness of the pharmaceutical treatment under evaluation for each separate one of the plurality of different prescription levels.

4. The method as defined in claim 3, wherein the step of determining a threshold level of compliance for each of the one or more constant prescription levels below which receiving the pharmaceutical treatment under evaluation at the respective prescription level results in an effect that is less desirable than an effect of not receiving the pharmaceutical treatment under evaluation includes determining a threshold level of compliance for each of the plurality of prescription levels.

5. The method as defined in claim 1,
   wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter at each of the plurality of different prescription levels at constant compliance level for each of the plurality of different compliance levels; and
   wherein the step of determining a potential effectiveness of the pharmaceutical treatment under evaluation on the target medical parameter includes determining the potential effectiveness of the pharmaceutical treatment under evaluation at each of the plurality of different prescription levels at each separate one of the plurality of different compliance levels.

6. The method as defined in claim 1,
   wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter indicating effects of consumption of the pharmaceutical treatment under evaluation by the plurality of patients at each of the plurality of different compliance levels at each of a plurality of different prescription levels for each separate one of a plurality of different pharmaceutical treatment dispensation times; and
   wherein the step of determining a potential effectiveness of the pharmaceutical treatment under evaluation on the target medical parameter includes determining the potential effectiveness of the pharmaceutical treatment under evaluation dispensed at each of a plurality of different prescription levels at each of the plurality of different pharmaceutical treatment dispensation times.

7. The method as defined in claim 1,
   wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter indicating effects of consumption of the pharmaceutical treatment under evaluation by the plurality of patients at each of the plurality of different compliance levels at constant prescription level for each of a plurality of different pharmaceutical treatment dispensation times; and
   wherein the step of determining a potential effectiveness of the pharmaceutical treatment under evaluation on the target medical parameter includes determining the potential effectiveness of the pharmaceutical treatment under evaluation dispensed at the constant prescription level at each of the plurality of different pharmaceutical treatment dispensation times.

8. The method as defined in claim 1, wherein the step of determining a potential effectiveness of the pharmaceutical treatment under evaluation on the target medical parameter includes:
   analyzing a trend related to the target medical parameter indicating effects of consumption of a pharmaceutical treatment under evaluation by the plurality of patients at constant prescription level at constant compliance level at each of a plurality of different pharmaceutical treatment dispensation times; and
   determining the potential effectiveness of the pharmaceutical treatment under evaluation dispensed at the constant prescription level at each separate one of the plurality of different pharmaceutical treatment dispensation times to thereby identify optimal dispensation times selection.

9. The method as defined in claim 1,
   wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter indicating effects of consumption of the pharmaceutical treatment under evaluation by the plurality of patients collectively having a plurality of different demographic factors at each of the plurality of different compliance levels at constant prescription level for each of a plurality of different prescription levels with respect to each separate one of the plurality of demographic factors; and
   wherein the step of determining a potential effectiveness of the pharmaceutical treatment under evaluation on the target medical parameter includes determining the potential effectiveness of the pharmaceutical treatment under evaluation at each of the plurality of different prescription levels with respect to each separate one of plurality of demographic factors.

10. The method as defined in claim 1, further comprising the steps of:
analyzing a trend related to the non-target medical parameter indicating effects of consumption of the pharmaceutical treatment under evaluation by the plurality of patients at the plurality of different pharmaceutical treatment compliance levels at each of the one or more constant prescription levels to thereby determine a correlation, when existing, between the trend related to the non-target medical parameter and compliance level associated with the respective one or more constant prescription levels for the pharmaceutical treatment under evaluation; and
determining a potential effectiveness of the pharmaceutical treatment under evaluation on the non-target target medical parameter at each of the one or more prescription levels responsive to a determination of an effect of compliance level on the pharmaceutical treatment under evaluation at each of the one or more constant prescription levels.

11. The method as defined in claim 1, further comprising the steps of:
performing an actual physical verification by a human observer that a patient consumed the pharmaceutical treatment under evaluation as prescribed; and
storing in memory of the computer, an indication of whether the respective patient self-administered the pharmaceutical treatment under evaluation as prescribed defining a compliance indication, the compliance indication comprising an indication of an actual physical verification by a human observer that the respective patient consumed the pharmaceutical treatment under evaluation as prescribed.

12. A method for computerized monitoring of effectiveness of pharmaceutical treatments under evaluation in patients, the method comprising the steps of:
receiving by a computer, data for each of a plurality of patients indicating whether the respective patient self-administered a pharmaceutical treatment under evaluation as prescribed to thereby document patient compliance with prescription instructions for the pharmaceutical treatment under evaluation; and
responsive to the received data, determining a potential effectiveness of the pharmaceutical treatment under evaluation on a target medical parameter, the step of determining a potential effectiveness of the pharmaceutical treatment under evaluation on the target medical parameter including the steps of:
analyzing a trend related to the target medical parameter indicating effects of consumption of the pharmaceutical treatment under evaluation by the plurality of patients at a plurality of different pharmaceutical treatment compliance levels at constant prescription level for each of a plurality of different prescription levels to thereby determine a correlation, when existing, between the trend related to the target medical parameter and compliance level associated with each respective prescription level for the pharmaceutical treatment under evaluation, and
determining a threshold level of compliance for each of the plurality of prescription levels below which receiving the pharmaceutical treatment under evaluation at the respective prescription level results in an effect on the target medical parameter that is less desirable than an effect of not receiving the pharmaceutical treatment under evaluation.

13. The method as defined in claim 12, wherein the step of determining the potential effectiveness of the pharmaceutical treatment under evaluation on the target medical parameter comprises the step of:
determining for each of the plurality of prescription levels, a minimum level of compliance necessary to have a positive effect on the target medical parameter exceeding that of not receiving the pharmaceutical treatment under evaluation.

14. The method as defined in claim 12, further comprising the steps of:
analyzing a trend related to the non-target medical parameter indicating effects of consumption of the pharmaceutical treatment under evaluation by the plurality of patients at the plurality of different pharmaceutical treatment compliance levels at each of the plurality of prescription levels to thereby determine a correlation, when existing, between the trend related to the non-target medical parameter and compliance level associated with each of the respective prescription levels for the pharmaceutical treatment under evaluation; and
determining a potential effectiveness of the pharmaceutical treatment under evaluation on the non-target target medical parameter at each of the plurality of prescription levels responsive to a determination of an effect of the plurality of different compliance levels on the pharmaceutical treatment under evaluation at each of the plurality of prescription levels.

15. A method for computerized monitoring of effectiveness of pharmaceutical treatments under evaluation in patients, the method comprising the steps of:
receiving by a computer, data for each of a plurality of patients indicating whether the respective patient self-administered a pharmaceutical treatment under evaluation as prescribed to thereby document patient compliance with prescription instructions for the pharmaceutical treatment under evaluation to define compliance data; and
responsive to the received data, determining a potential effectiveness of the pharmaceutical treatment under evaluation on a target medical parameter, the step of determining a potential effectiveness of the pharmaceutical treatment under evaluation on the target medical parameter including the step of:
analyzing a trend related to the target medical parameter indicating effects of consumption of the pharmaceutical treatment under evaluation by the plurality of patients at a plurality of different pharmaceutical treatment compliance levels at each of one or more constant prescription levels to thereby determine a correlation, when existing, between the trend related to the target medical parameter and compliance level associated with the respective one or more constant prescription levels for the pharmaceutical treatment under evaluation,
determining an effect of compliance level on effectiveness of the pharmaceutical treatment under evaluation at each of the one or more constant prescription levels,
determining for each of the one or more constant prescription levels, a threshold level of compliance below which receiving the pharmaceutical treatment under evaluation at the respective prescription level results in an effect that is less desirable than an effect of not receiving the pharmaceutical treatment under evaluation, and determining for each of the one or more constant prescription levels, a minimum level of compliance necessary to have a positive effect on the target medical parameter exceeding that of not receiving the pharmaceutical treatment under evaluation.

16. The method as defined in claim 15,
wherein the step of analyzing a trend related to the target medical parameter indicating effects of consumption of a pharmaceutical treatment under evaluation by the plurality of patients at a plurality of different pharmaceutical treatment compliance levels at each of one or more constant prescription levels includes analyzing a trend related to the target medical parameter at each of the plurality of different compliance levels at constant prescription level for each of a plurality of different prescription levels; and
wherein the step of determining a potential effectiveness of the pharmaceutical treatment under evaluation on the target medical parameter includes determining the potential effectiveness of the pharmaceutical treatment under evaluation for each separate one of the plurality of different prescription levels.

17. Computer readable code of program instructions stored on a tangible program storage device readable by a computer, that when executed by the computer, cause the computer to perform operations for computerized monitoring of effectiveness of pharmaceutical treatments under evaluation, the operations comprising:
    receiving a data entry for each separate one of a plurality of patients and for each medication administration event, each data entry comprising an indication of whether a patient self-administered the pharmaceutical treatment under evaluation as prescribed to define compliance data to thereby document in a prescription compliance record of each specific patient, information about a frequency in which the patient complied with prescription instructions for the pharmaceutical treatment under evaluation;
    storing the compliance data for each respective patient in a prescription compliance record of the respective patient;
    responsive to the compliance data for each of the plurality of patients, providing data to graphically display to a provider a trend related to a target medical parameter indicating effects of consumption of the pharmaceutical treatment under evaluation by the plurality of patients at a plurality of different pharmaceutical treatment compliance levels at each of one or more constant prescription levels;
    storing correlations between the trend related to the target medical parameter and compliance level associated with the respective one or more constant prescription levels for the pharmaceutical treatment under evaluation, when existing, responsive to identification of the correlations by the provider;
    providing data to graphically display an indication of a presently identified correlation between a trend related to the target medical parameter and compliance frequency for the pharmaceutical treatment under evaluation to thereby aid a provider to determine a threshold level of compliance for each of the one or more constant prescription levels below which receiving the pharmaceutical treatment under evaluation at the respective prescription level results in an effect that is less desirable than an effect of not receiving the pharmaceutical treatment under evaluation; and
    responsive to provider analysis of the presently identified correlation, storing an indication of the threshold level of compliance for each of the one or more constant prescription levels below which receiving the pharmaceutical treatment under evaluation at the respective prescription level results in an effect that is less desirable than an effect of not receiving the pharmaceutical treatment under evaluation.

18. Computer program code of program instructions as defined in claim 17, wherein the operations further comprise:
    storing an indication of a minimum level of compliance necessary to have a positive effect on the target medical parameter exceeding that of not receiving the pharmaceutical treatment under evaluation for each of the one or more constant prescription levels responsive to provider analysis of a respective presently identified correlation at each of the of the one or more constant prescription levels.

19. Computer program code of program instructions as defined in claim 17,
wherein the operation of providing data to graphically display to a provider a trend related to a target medical parameter indicating effects of consumption of the pharmaceutical treatment under evaluation by the plurality of patients at a plurality of different pharmaceutical treatment compliance levels at each of one or more constant prescription levels is performed for each separate one of a plurality of different prescription levels; and
wherein the operation of storing an indication of the threshold level of compliance for each of the one or more constant prescription levels below which receiving the pharmaceutical treatment under evaluation at the respective prescription level results in an effect that is less desirable than an effect of not receiving the pharmaceutical treatment under evaluation includes storing an indication of the threshold level of compliance for each separate one of the plurality of constant prescription levels.

20. Computer program code of program instructions as defined in claim 17, wherein the operations further comprise:
    providing data to graphically display a trend related to a non-target medical parameter indicating effects of consumption of the pharmaceutical treatment under evaluation by the plurality of patients at a plurality of different pharmaceutical treatment compliance levels at each of one or more constant prescription levels to facilitate identifying a correlation, when existing, between the trend related to the non-target medical parameter and compliance level associated with the respective one or more constant prescription levels for the pharmaceutical treatment under evaluation and determining a potential effectiveness of the pharmaceutical treatment under evaluation on the non-target target medical parameter at each of the one or more prescription levels responsive to a determination of an effect of compliance level on the pharmaceutical treatment under evaluation at each of the one or more constant prescription levels; and
    storing an indication of the potential effectiveness of the pharmaceutical treatment under evaluation on the non-target target medical parameter at each of the one or more prescription levels responsive to the determination of an effect of compliance level on the pharmaceutical treatment under evaluation at each of the one or more constant prescription levels.

* * * * *